(12) United States Patent
Shiffman et al.

(10) Patent No.: US 12,025,610 B2
(45) Date of Patent: Jul. 2, 2024

(54) METHODS FOR QUANTITATION OF INSULIN AND C-peptide

(71) Applicant: Quest Diagnostics Investments LLC, Secaucus, NJ (US)

(72) Inventors: Dov Shiffman, Palo Alto, CA (US); Carmen Tong, Dublin, CA (US); James J. Devlin, Lafayette, CA (US); Michael J. McPhaul, Capistrano Beach, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 582 days.

(21) Appl. No.: 17/234,448

(22) Filed: Apr. 19, 2021

(65) Prior Publication Data

US 2022/0042971 A1    Feb. 10, 2022

Related U.S. Application Data

(63) Continuation of application No. 15/942,188, filed on Mar. 30, 2018, now Pat. No. 10,983,108.
(Continued)

(51) Int. Cl.
*G01N 33/49* (2006.01)
*G01N 30/72* (2006.01)
(Continued)

(52) U.S. Cl.
CPC ....... *G01N 33/492* (2013.01); *G01N 30/7266* (2013.01); *G01N 33/6848* (2013.01);
(Continued)

(58) Field of Classification Search
CPC ......... G01N 2333/62; G01N 2800/042; G01N 2800/50; G01N 30/7266; G01N 33/492; G01N 33/6848; G01N 33/74
See application file for complete search history.

(56) References Cited

U.S. PATENT DOCUMENTS 5,772,874 A    6/1998   Quinn et al.
5,795,469 A    8/1998   Quinn et al.
(Continued)

FOREIGN PATENT DOCUMENTS

CN    103392219 A    11/2013
CN    103454433 A    12/2013
(Continued)

OTHER PUBLICATIONS

Stocklin R., et al., "A Stable Isotope Dilution Assay for the in Vivo Determination of Insulin Levels in Humans by Mass Spectrometry," Diabetes, 1997, vol. 46 (1), pp. 44-50.
(Continued)

*Primary Examiner* — Jennifer Wecker
(74) *Attorney, Agent, or Firm* — Foley & Lardner LLP

(57) ABSTRACT

Methods are described for diagnosing or prognosing insulin resistance in diabetic and pre-diabetic patients, the method comprising determining the amount of insulin and C-peptide in a sample. Provided herein are mass spectrometric methods for detecting and quantifying insulin and C-peptide in a biological sample utilizing enrichment and/or purification methods coupled with tandem mass spectrometric or high resolution/high accuracy mass spectrometric techniques.

37 Claims, 20 Drawing Sheets

Specification includes a Sequence Listing.

Related U.S. Application Data

(60) Provisional application No. 62/644,378, filed on Mar. 16, 2018, provisional application No. 62/480,029, filed on Mar. 31, 2017.

(51) Int. Cl.
  *G01N 33/68* (2006.01)
  *G01N 33/74* (2006.01)
(52) U.S. Cl.
  CPC ......... *G01N 33/74* (2013.01); *G01N 2333/62* (2013.01); *G01N 2800/042* (2013.01); *G01N 2800/50* (2013.01)

(56) References Cited

U.S. PATENT DOCUMENTS

| | | | |
|---|---|---|---|
| 5,919,368 | A | 7/1999 | Quinn et al. |
| 5,968,367 | A | 10/1999 | Quinn et al. |
| 6,107,623 | A | 8/2000 | Bateman et al. |
| 6,124,137 | A | 9/2000 | Hutchens et al. |
| 6,204,500 | B1 | 3/2001 | Whitehouse et al. |
| 6,268,144 | B1 | 7/2001 | Koester |
| 6,995,364 | B2 | 2/2006 | Makarov et al. |
| 10,324,082 | B2 | 6/2019 | Taylor et al. |
| 2005/0103991 | A1 | 5/2005 | Walk et al. |
| 2006/0219558 | A1 | 10/2006 | Hafeman et al. |
| 2008/0118932 | A1 | 5/2008 | Toler et al. |
| 2009/0035807 | A1 | 2/2009 | McCellan et al. |
| 2009/0090856 | A1 | 4/2009 | Grant et al. |
| 2010/0130402 | A1 | 5/2010 | Pfuetzner et al. |
| 2011/0166132 | A1 | 7/2011 | Hitchcock et al. |
| 2012/0164741 | A1 | 6/2012 | Chen et al. |
| 2013/0177544 | A1* | 7/2013 | Stoll ................ A61P 13/12 424/94.1 |
| 2013/0344048 | A1 | 12/2013 | Wasserman et al. |
| 2015/0346183 | A1 | 12/2015 | Clarke et al. |
| 2015/0362510 | A1 | 12/2015 | Gall et al. |
| 2016/0282328 | A1* | 9/2016 | Taylor ................ G01N 33/6848 |
| 2016/0357935 | A1* | 12/2016 | Pottala .................... G01N 33/92 |
| 2018/0020947 | A1 | 1/2018 | Cistola et al. |

FOREIGN PATENT DOCUMENTS

| | | |
|---|---|---|
| JP | 2004503749 A | 2/2004 |
| JP | 2005526962 A | 9/2005 |
| JP | 2008540573 A | 11/2008 |
| JP | 2009540856 A | 11/2009 |
| JP | 6092890 B2 | 3/2017 |
| WO | 0204957 A2 | 1/2002 |
| WO | 2006124713 A2 | 11/2006 |
| WO | 2008001079 A1 | 1/2008 |
| WO | 2009133152 A1 | 11/2009 |
| WO | 2012092281 A2 | 7/2012 |
| WO | 2014105858 A1 | 7/2014 |
| WO | 2016141204 A1 | 9/2016 |

OTHER PUBLICATIONS

Taylor S.W., et al., "A High-throughput Mass Spectrometry Assay to Simultaneously Measure Intact Insulin and C-peptide," Clinica Chimica Acta, 2016, vol. 455, pp. 202-208.

Thevis M., et al., "Current Role of LC-MS(/MS) in Doping Control," Analytical and Bioanalytical Chemistry, 2007, vol. 388 (7), pp. 1351-1358.

Thevis M., et al., "Doping Control Analysis of Intact Rapid-Acting Insulin Analogues in Human Urine by Liquid Chromatography-Tandem Mass Spectrometry," Analytical Chemistry, 2006, vol. 78 (6), pp. 1897-1903.

Thevis M., et al., "Mass Spectrometric Determination of Insulins and Their Degradation Products in Sports Drug Testing," Mass Spectrometry Reviews, 2008, vol. 27 (1), pp. 35-50.

Thevis M., et al., "Qualitative Determination of Synthetic Analogues of Insulin in Human Plasma by Immunoaffinity Purification and Liquid Chromatography-Tandem Mass Spectrometry for Doping Control Purposes," Analytical Chemistry, Jun. 2005, vol. 77 (11), pp. 3579-3585. http://dx.doi.org/10.1021/ac050066i.

Thevis M., et al., "Recommended Criteria for the Mass Spectrometric Identification of Target Peptides and Proteins (8 kDa) in Sports Drug Testing," Rapid Communications in Mass Spectrometry, 2007, vol. 21, pp. 297-304.

Thomas A., et al., "Identification and Determination of Human Insulin, Synthetic Insulin Analogues, Their Degradation Products and C-peptide in Human Urine and Human Plasma for Doping Control Purposes by Means of Liquid Chromatography / Mass Spectrometry", University and State Library Bonn, 2008, pp. 1-154— English Translation Available.

Thomas A., et al., "Mass Spectrometric Determination of Gonadotrophin-Releasing Hormone (Gnrh) In Human Urine for Doping Control Purposes by Means of LC-ESI-MS/MS," Journal of Mass Spectrometry, 2008, vol. 43 (7), pp. 908-915.

Thomas A., et al., "Mass Spectrometric Identification of Degradation Products of Insulin and Its Long-Acting Analogues in Human Urine for Doping Control Purposes," Analytical Chemistry, 2007, vol. 79 (6), pp. 2518-2524.

Van-Uytfanghe K., et al., "New Liquid Chromatography/ Electrospray Ionization Tandem Mass Spectrometry Measurement Procedure for Quantitative Analysis of Human Insulin In Serum," Rapid Communications in Mass Spectrometry, 2007, vol. 21 (5), pp. 819-821.

Waters QTOF Ultima ESI, Mass Spectrometry Lab, School of Chemical Sciences, 2002, 2 pages. [retrieved on May 18, 2018]. Retrieved from the Internet:[URL: http://www.scs.illinois.edu/massSpec/instrum/qtof.php].

Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.

Written Opinion for Application No. PCT/US11/67397, dated Jun. 28, 2012, 6 Pages.

Zhang X., et al., "Apparent Gas-Phase Acidities of Multiply Protonated Peptide Ions: Ubiquitin, Insulin B, and Renin Substrate," Journal of the American Society for Mass Spectrometry, Dec. 1996, vol. 7 (12), pp. 1211-1218.

Zimmer D., et al., "Comparison of Turbulent-Flow Chromatography with Automated Solid-Phase Extraction in 96-Well Plates and Liquid-Liquid Extraction Used As Plasma Sample Preparation Techniques for Liquid Chromatograph—Tandem Mass Spectrometry," Journal of Chromatography A, 1999, vol. 854, pp. 23-35.

Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.

Bredehoft M., et al., "Quantification of Human Insulin-Like Growth Factor-1 and Qualitative Detection of Its Analogues in Plasma Using Liquid Chromatography/Electrospray Ionisation Tandem Mass Spectrometry," Rapid Communications in Mass Spectrometry, 2008, vol. 22 (4), pp. 477-485.

Cham B.E., et al., "A Solvent System for Delipidation of Plasma or Serum Without Protein Precipitation," Journal of Lipid Research, Mar. 1976, vol. 17 (2), pp. 176-181. https://www.jlr.org/content/17/2/176.full.pdf+html?sid=b129fd28-cfcb-4630-b11c-d4ca4c010a8a.

Darby S.M., et al., "A Mass Spectrometric Method for Quantitation of Intact Insulin in Blood Samples," Journal of Analytical Toxicology , 2001, vol. 25 (1), pp. 8-14.

European Search Report for Application No. 16759509.9 dated Jul. 13, 2018.

European Search Report for Application No. 17189034.6 dated Oct. 19, 2017.

Ewing N.P., et al., "Effects of Cysteic Acid Groups on the Gas-Phase Reactivity and Dissociation of [M+4H](4+) Ions From Insulin Chain B," Journal of the American Society for Mass Spectrometry, Oct. 1999, vol. 10 (10), pp. 928-940.

(56) References Cited

OTHER PUBLICATIONS

Extended European Search Report for Application No. EP18209927. 5, dated Apr. 17, 2019, 8 pages.
Extended European Search Report for Application No. 11852467.7, dated Mar. 14, 2014, 6 pages.
Extended European Search Report for Application No. 18777247.0, dated Oct. 7, 2020.
Extended European Search Report for Application No. EP16176190. 3, dated Sep. 29, 2016, 7 pages.
Fierens C., et al., "Strategies for Determination of Insulin with Tandem Electrospray Mass Spectrometry: Implications for Other Analyte Proteins?," Rapid Communications in Mass Spectrometry, 2001, vol. 15 (16), pp. 1433-1441.
Final Office Action dated Aug. 3, 2016 for U.S. Appl. No. 13/338,123, filed Dec. 27, 2011.
Final Office Action dated Oct. 12, 2018 for U.S. Appl. No. 13/338,123, filed Dec. 27, 2011.
Final Office Action dated Jul. 27, 2020 for U.S. Appl. No. 15/942,188, filed Mar. 30, 2018.
Fung, Y.M.E., et al., "Facile Disulfide Bond Cleavage in Gaseous Peptide and Protein Cations by Ultraviolet Photodissociation at 157nm," Angewandte Chemie International Edition, 2005, vol. 44(39), pp. 6399-6403.
Guedes S., et al., "Mass Spectrometry Characterization of the Glycation Sites of Bovine Insulin by Tnadem Mass Spectrometry," Journal of the American Society for Mass Spectrometry, 2009, vol. 20 (7), pp. 1319-1326.
Ho E.N.M., et al., "Doping Control Analysis of Insulin and Its Analogues in Equine Plasma by Liquid Chromatography—Tandem Mass Spectrometry," Journal of Chromatography A, 2008, vol. 1201, pp. 183-190.
International Preliminary Report and Written Opinion on Patentability for Application No. PCT/US2016/020723, dated Sep. 14, 2017.
International Preliminary Report on Patentability for Application No. PCT/US2011/067397, dated Jul. 11, 2013.
International Search Report and Written Opinion for Application No. PCT/US2016/020723, dated Jul. 25, 2016, 19 pages.
International Search Report for Application No. PCT/US11/67397, dated Jun. 28, 2012, 6 Pages.
Jespersen S., et al., "Optimization of Sample Recovery From the Nitrocellulose Support Used in Plasma Desorption Mass Spectrometry and Its Use for Multiple Analyses of Insulin," Biological Mass Spectrometry, Jan. 1993, vol. 22 (1), pp. 77-83.
Jia X., et al., "Structural and Functional Changes in Human Insulin Induced by Methylglyoxal," FASEB Journal, 2006, vol. 20 (9), pp. E871-E879.
Jonassen P., et al., "Single-Step Trypsin Cleavage of a Fusion Protein to Obtain Human Insulin and Its C Peptide," European Journal of Biochemistry, Mar. 1996, vol. 236 (2), pp. 656-661.
Kippen A.D., et al., "Development of an Isotope Dilution Assay for Precise Determination of Insulin, C-Peptide, and Proinsulin Levels in Non-diabetic and Type II Diabetic Individuals With Comparison to Immunoassay," The Journal of Biological Chemistry, May 1997, vol. 272 (19), pp. 12513-12522. XP002272400.
Kuuranne T., et al., "Insulins in Equine Urine: Qualitative Analysis by Immunoaffinity Purification and Liquid Chromatography/ Tandem Mass Spectrometry for Doping Control Purposes in Horse-Racing," Rapid Communications in Mass Spectrometry, 2008, vol. 22 (3), pp. 355-362. http://dx.doi.org/10.1002/rcm.3360.
Landreh M., et al., "Proinsulin C-Peptide Interferes With Insulin Fibril Formation," Biochemical and Biophysical Research Communications, Feb. 2012, vol. 418 (3), pp. 489-493. https://www.sciencedirect.com/science/article/pii/S0006291X12000745.
Landreh M., et al., "Insulin, Islet Amyloid Polypeptide and C-Peptide Interactions Evaluated by Mass Spectrometric Analysis: Interactions of Insulin, IAPP and C-peptide in ESI-MS," Rapid Communications in Mass Spectrometry, 2014, vol. 28 (2), pp. 178-184. XP55490228.

Le-Breton M.H., et al., "Direct Determination of Recombinant Bovine Somatotropin in Plasma from A Treated Goat by Liquid Chromatography/High-Resolution Mass Spectrometry," Rapid Communications in Mass Spectrometry, 2008, vol. 22 (20), pp. 3130-3136.
Loo J.A., et al., "Tandem Mass Spectrometry of Very Large Molecules: Serum Albumin Sequence Information From Multiply Charged Ions Formed by Electrospray Ionization," Analytical Chemistry, 1991, vol. 63 (21), pp. 2488-2499.
Manley S., et al., "Comparison of II Human Insulin Assays: Implications for Clinical Investigation and Research," Clinical Chemistry, 2007, vol. 53 (5), pp. 922-932.
Mannering S.I., et al., "The Insulin A-Chain Epitope Recognized by Human T Cells is Posttranslationally Modified," The Journal of Experimental Medicine, 2005, vol. 202 (9), pp. 1191-1197.
Merchant M., et al., "Recent Advancements in Surface-Enhanced Laser Desorption/Ionization-Time of Flight-Mass Spectrometry," Electrophoresis, 2000, vol. 21 (6), pp. 1164-1167.
Non-Final Office Action dated May 23, 2018 for U.S. Appl. No. 15/059,247, filed Mar. 2, 2016.
Non-Final Office Action dated Jan. 14, 2020 for U.S. Appl. No. 15/942,188, filed Mar. 30, 2018.
Non-Final Office Action dated Dec. 22, 2017 for U.S. Appl. No. 13/338,123, filed Dec. 27, 2011.
Non-Final Office Action dated Jan. 22, 2016 for U.S. Appl. No. 14/063,956, filed Oct. 25, 2013.
Non-Final Office Action dated Dec. 24, 2014 for U.S. Appl. No. 13/338,123, filed Dec. 27, 2011.
Non-Final Office Action dated Dec. 24, 2015 for U.S. Appl. No. 13/338,123, filed Dec. 27, 2011.
Olsen J.V., et al., "Higher-Energy C-Trap Dissociation for Peptide Modification Analysis," Nature Methods, 2007, vol. 4 (9), pp. 709-712.
Peng, I.X., et al., "Reactive-Electrospray-Assisted Laser Desorption/ Ionization for Characterization of Peptides and Proteins," Analytical chemistry, ACS Publications, Aug. 2008, vol. 80(18), pp. 6995-7003.
Regnier F., et al., "Future Potential of Targeted Component Analysis by Multidimensional Liquid Chromatography-Mass Spectrometry," Journal of Chromatography A, 1996, vol. 750, pp. 3-10.
Requirement for Restriction dated Nov. 5, 2015 for U.S. Appl. No. 13/338,123, filed Dec. 27, 2011.
Robb D.B., et al., "Atmospheric Pressure Photoionization: An Ionization Method for Liquid Chromatography—Mass Spectrometry," Analytical Chemistry, 2000, vol. 72 (15), pp. 3653-3659.
Rodriguez-Cabaleiro D., et al., "Pilot Study for the Standardization of Insulin Immunoassays with Isotope Dilution-Liquid Chromatography/ Tandem Mass Spectrometry," Clinical Chemistry, 2007, vol. 53 (8), pp. 1462-1469.
Schenk S., et al., "A High Confidence, Manually Validated Human Blood Plasma Protein Reference Set," BMC Medical Geonomics, 2008, vol. 1, pp. 41.
Sinner et al., "A Robust and Easy Method for Simultaneous Quantitation of Glucose and [6,6-d2]Glucose in Human Plasma Using GC-MS," Proceedings of the 52nd ASMS Conference on Mass Spectrometry and Allied Topics, Nashville, Tennessee, May 23-27, 2004, 5 pages.
Stephenson J. L., et al., "Ion Trap Collisional Activation of Disulfide Linkage Intact and Reduced Multiply Protonated Polypeptides," Rapid communications in Mass Spectrometry, 1999, vol. 13 (20), pp. 2040-2048.
Stewart K.W., et al., "A Simple and Rapid Method for Identifying and Semi-quantifying Peptide Hormones in Isolated Pancreatic Islets by Direct-Tissue Matrix-Assisted Laser Desorption Ionization Time-of-Flight Mass Spectrometry: Detection of Pancreatic Islet Peptides by Direct-Tissue MALDI-TOF MS," Rapid Communications in Mass Spectrometry, Oct. 2011, vol. 25 (22), pp. 3387-3395. XP55490236.
Extended European Search Report for Application No. 22207995.6, dated May 7, 2023, 8 pages.

(56) References Cited

OTHER PUBLICATIONS

Marchesini, et al., "Nash: From Liver Diseases to Metabolic Disorders and Back to Clinical Hepatology," Hepatology (Baltimore, Md.), 2002, vol. 35 (2), pp. 497-4.

* cited by examiner

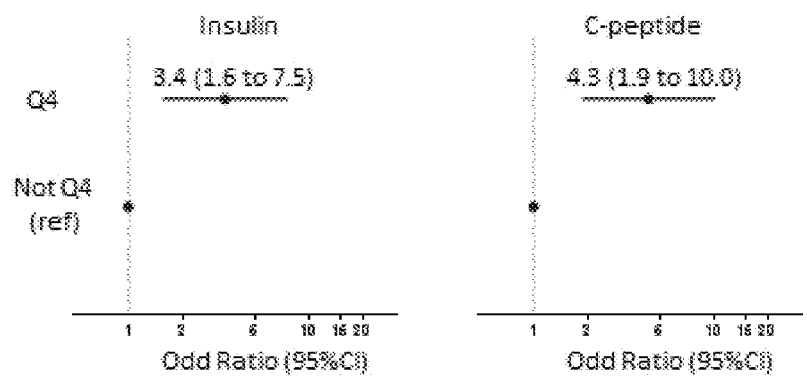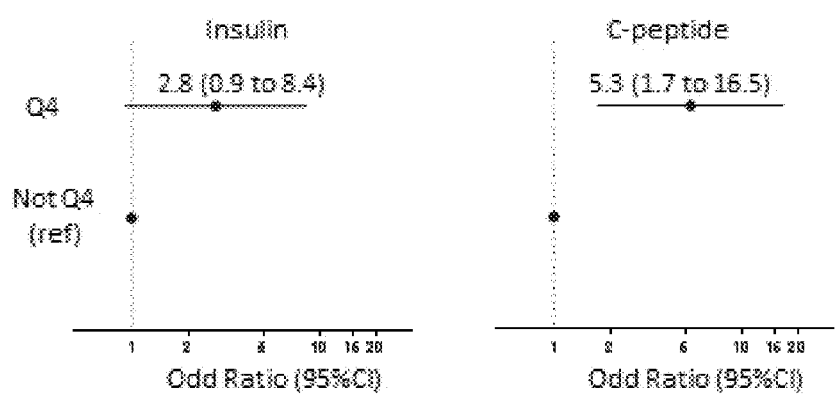

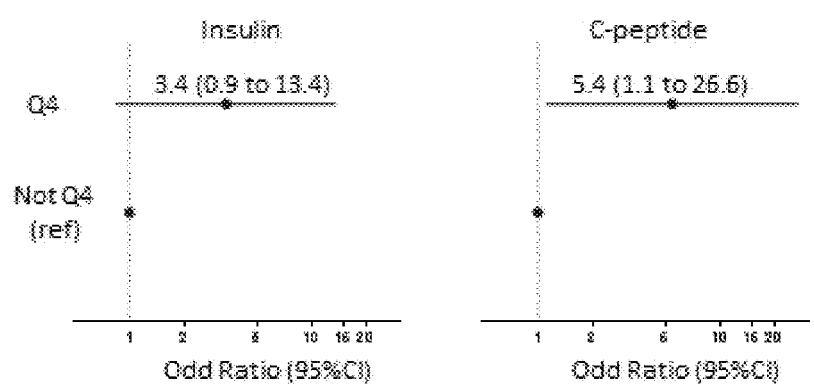

B-Chain (SEQ ID NO: 1) A-Chain (SEQ ID NO: 2)

B-Chain (SEQ ID NO: 1) A-Chain (SEQ ID NO: 2)

FIGURE 9
(SEQ ID NO: 3)
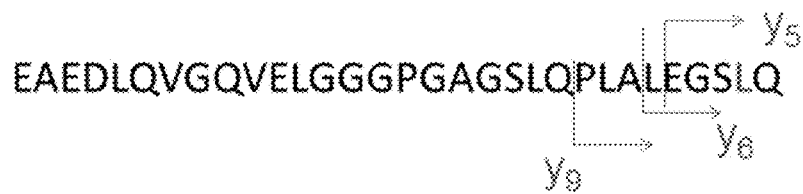
C pep heavy IS L=[15N,13C6 Leu]
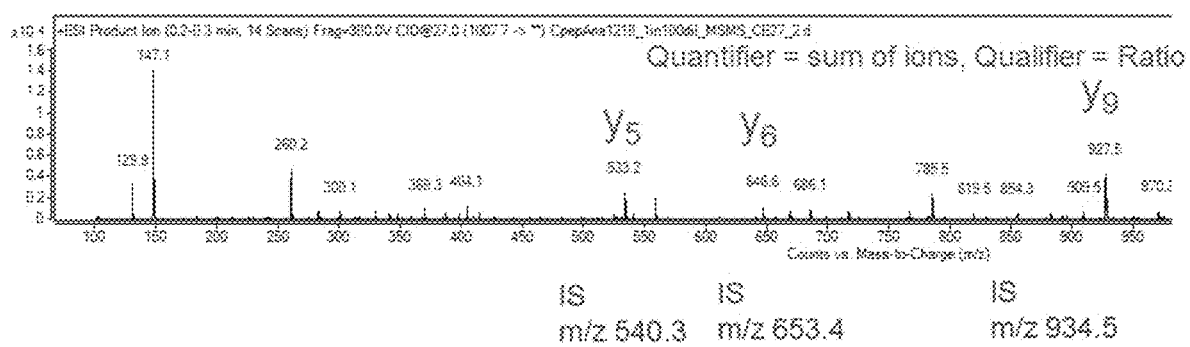

FIGURE 12

|  | Insulin (μIU/mL)* | | | C-peptide (ng/mL) | | |
|---|---|---|---|---|---|---|
|  | QC Low | QC Medium | QC High | QC Low | QC Medium | QC High |
| Target | 13.3 | 43.1 | 172.7 | 0.48 | 2.07 | 7.70 |
| Overall Mean | 14.1 | 43.3 | 173.0 | 0.51 | 1.96 | 7.77 |
| Overall SD | 1.5 | 3.6 | 12.7 | 0.05 | 0.14 | 0.35 |
| Overall CV | 11% | 8% | 7% | 10% | 7% | 5% |
| Overall Accuracy | 106% | 100% | 100% | 106% | 95% | 101% |

FIGURE 16

| | |
|---|---|
| Specimen Type | Serum Red Top (no gel) & SST are acceptable. Plasma is unacceptable |
| Intra Assay Precision | 4 – 9% |
| Inter Assay Precision | 7 – 11% |
| Recovery Study | Average range of recovery for insulin spiked patient samples was 96 – 106% at 10, 20 and 40 µIU/mL, respectively |
| Analytical Sensitivity (Limit of Quantitation) | 2.5 µIU/mL. Assay will report in whole numbers; LOQ = 3 µIU/mL. |
| Analytical Specificity (Cross Reactivity) | Humulin ® (Recombinant Human Insulin) (100%) - Identical to endogenous insulin |
| Analytical Specificity (Interference) | Hemolysis, Humalog ® (Insulin lispro) |
| Analytical Measurement Range (AMR) | 3-320 µIU/mL |
| Reference Interval Range | 16 µIU/mL or less |

FIGURE 17

| | |
|---|---|
| Specimen Type | Serum Red Top (no gel) & SST are acceptable. Plasma is unacceptable. |
| Intra Assay Precision | 4-8% |
| Inter Assay Precision | 7-10% |
| Recovery Study | Average range of recovery for C-peptide spiked into patient samples was 91 to 104% at 1.02, 1.70 and 3.40 ng/mL, respectively. |
| Analytical Sensitivity (Limit of Quantitation) | 0.11 ng/mL |
| Analytical Specificity (Cross Reactivity) | None detected |
| Analytical Specificity (Interference) | Gross hemolysis (slight or moderate hemolysis is acceptable) |
| Analytical Measurement Range (AMR) | 0.11-27.20 ng/mL |
| Reference Interval Range | 0.68 - 2.16 ng/mL |

|  |  | Normal Range |
| --- | --- | --- |
| Insulin | 18 uIU/ml | ≤15 |
| C-peptide | 2.55 ng/ml | 0.61 to 2.40 |
| Insulin resistance score | 86 | 1 to 66 |

A score below 33 is optimal. The insulin resistance score correlates with steady state glucose levels achieved during an insulin suppression test, a standard research test for insulin resistance. The score is based on insulin and C-peptide results.

SEQUENCE LISTING

<160> NUMBER OF SEQ ID NOS: 3

<210> SEQ ID NO 1
<211> LENGTH: 30
<212> TYPE: PRT
<213> ORGANISM: Homo sapiens

```
<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 31
<212> TYPE: PRT
<213> ORGANISM: Homo sapiens

<400> SEQUENCE: 3

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30
```

METHODS FOR QUANTITATION OF INSULIN AND C-peptide

CROSS-REFERENCE TO RELATED APPLICATIONS

This application is a continuation of U.S. Non-Provisional application Ser. No. 15/942,188, filed Mar. 30, 2018, issued as U.S. Pat. No. 10,983,108, which claims the benefit under 35 U.S.C. § 119(e) to U.S. Provisional Application Ser. No. 62/480,029, filed Mar. 31, 2017, and U.S. Provisional Application Ser. No. 62/644,378, filed Mar. 16, 2018, the contents of which are incorporated by reference in their entirety into the present disclosure.

BACKGROUND OF THE INVENTION

Insulin resistance varies several-fold in an apparently healthy population, and somewhere between one-fourth and one-third of the most insulin resistant of these individuals is at increased risk to develop a cluster of metabolic abnormalities and associated clinical syndromes. Direct estimates of insulin-mediated glucose disposal are impractical at a clinical level. However, plasma insulin concentrations are highly correlated with direct measures of insulin-mediated glucose disposal, and this has led to the introduction of several surrogate estimates of insulin resistance based on measurements of plasma insulin and glucose concentrations. Unfortunately, there is not a standardized insulin assay. As a consequence, it has not been possible to establish a universally applicable numerical cut-point with which to identify apparently healthy individuals who are sufficiently insulin resistant to be at high risk for a number of adverse clinical outcomes.

In response to this dilemma, a number of surrogate markers based on commonly measured metabolic abnormalities associated with IR have been proposed to help identify insulin resistant individuals prior to development of manifest disease. For example, a diagnosis of the metabolic syndrome (MetS) is an example of this approach. Although a diagnosis of the MetS is associated with a direct measure of insulin-mediated glucose disposal, only approximately 50% of the one-third of the most insulin resistant population of apparently healthy persons qualified for a diagnosis of the MetS.

A reliable and accurate method for identifying insulin resistance is needed.

SUMMARY OF THE INVENTION

In one aspect, provided herein are methods for diagnosing or prognosing insulin resistance in diabetic and pre-diabetic patients, the method comprising for measuring insulin and c-peptide levels in a patient by determining the amount of insulin and C-peptide in a sample.

In certain embodiments, the methods provided herein comprise multiplexed assays that simultaneously measure the amount of insulin and C-peptide in a sample by mass spectrometry. In some embodiments, methods comprise (a) subjecting insulin and C-peptide from a sample to an ionization source under conditions suitable to generate one or more insulin and C-peptide ions detectable by mass spectrometry; and (b) determining the amount of one or more insulin and C-peptide ions by mass spectrometry.

In some embodiments, insulin resistance is diagnosed if insulin value determined by the mass spectrometry method described herein is greater than or equal to 7 µIU/mL. In some embodiments, insulin resistance is diagnosed if insulin value determined by the mass spectrometry method described herein is greater than or equal to 8 µIU/mL. In some embodiments, insulin resistance is diagnosed if insulin value determined by the mass spectrometry method described herein is greater than or equal to 9 µIU/mL. In some embodiments, insulin resistance is diagnosed if insulin value determined by the mass spectrometry method described herein is greater than or equal to 10 µIU/mL. In some embodiments, insulin resistance is diagnosed if insulin value determined by the mass spectrometry method described herein is greater than or equal to 11 µIU/mL. In some embodiments, insulin resistance is diagnosed if insulin value determined by the mass spectrometry method described herein is greater than or equal to 12 µIU/mL. In some embodiments, insulin resistance is diagnosed if insulin value determined by the mass spectrometry method described herein is greater than or equal to 13 µIU/mL. In some embodiments, insulin resistance is diagnosed if insulin value determined by the mass spectrometry method described herein is greater than or equal to 14 µIU/mL. In some embodiments, insulin resistance is diagnosed if insulin value determined by the mass spectrometry method described herein is greater than or equal to 15 µIU/mL.

In a preferred embodiment, insulin resistance is diagnosed if insulin value determined by the mass spectrometry method described herein is greater than or equal to 15 µIU/mL.

In some embodiments, insulin resistance is diagnosed if C-peptide value determined by the mass spectrometry method described herein is greater than or equal to 1.4 ng/mL. In some embodiments, insulin resistance is diagnosed if C-peptide value determined by the mass spectrometry method described herein is greater than or equal to 1.5 ng/mL. In some embodiments, insulin resistance is diagnosed if C-peptide value determined by the mass spectrometry method described herein is greater than or equal to 1.6 ng/mL. In some embodiments, insulin resistance is diagnosed if C-peptide value determined by the mass spectrometry method described herein is greater than or equal to 1.7 ng/mL. In some embodiments, insulin resistance is diagnosed if C-peptide value determined by the mass spectrometry method described herein is greater than or equal to 1.8 ng/mL. In some embodiments, insulin resistance is diagnosed if C-peptide value determined by the mass spectrometry method described herein is greater than or equal to 1.9 ng/mL. In some embodiments, insulin resistance is diagnosed if C-peptide value determined by the mass spectrometry method described herein is greater than or equal to 2 ng/mL. In some embodiments, insulin resistance is diagnosed if C-peptide value determined by the mass spectrometry method described herein is greater than or equal to 2.1 ng/mL. In some embodiments, insulin resistance is diagnosed if C-peptide value determined by the mass spectrometry method described herein is greater than or equal to 2.2 ng/mL. In some embodiments, insulin resistance is diagnosed if C-peptide value determined by the mass spectrometry method described herein is greater than or equal to 2.3 ng/mL. In some embodiments, insulin resistance is diagnosed if C-peptide value determined by the mass spectrometry method described herein is greater than or equal to 2.4 ng/mL.

In a preferred embodiment, insulin resistance is diagnosed if C-peptide value determined by the mass spectrometry method described herein is greater than or equal to 2.4 ng/mL.

In some embodiments, an insulin resistance score (RS) and/or probability of developing insulin resistance, P(IR), is provided herein based on the levels of insulin and C-peptide measured by methods provided herein.

In some embodiments, insulin resistance score (RS) and/or probability of developing insulin resistance, P(IR), is determined by the following:

$$RS = (\text{Insulin} \times 0.0295) + (\text{C-peptide} \times 0.00372)$$

$$P(IR) = \frac{e^{-4.5046+1.0001 \times RS}}{1 + e^{-4.5046+1.0001 \times RS}}$$

In some embodiments, an insulin resistance score (RS) and/or probability of developing insulin resistance, P(IR), is provided herein based on the levels of insulin and C-peptide measured by methods provided herein and creatine measured by standard methods.

In some embodiments, insulin resistance score (RS) and/or probability of developing insulin resistance, P(IR), is determined by the following:

$$RS = (\text{Insulin} \times 0.0265) + (\text{C-peptide} \times 0.00511) + (\text{Creatinine} \times -3.2641)$$

$$P(IR) = \frac{e^{-2.2626+1.0005 \times RS}}{1 + e^{-2.2626+1.0005 \times RS}}$$

In some embodiments, an insulin resistance score (RS) and/or probability of developing insulin resistance, P(IR), is provided herein based on the levels of insulin and C-peptide measured by methods provided herein and creatine, triglyceride (TG)/HDL-C, and BMI measured by standard methods.

In some embodiments, insulin resistance score (RS) and/or probability of developing insulin resistance, P(IR), is determined by the following:

$$RS = (\text{Insulin} \times 0.0227) +$$
$$(\text{C-peptide} \times 0.0046) + (\text{Creatinine} \times -3.5553) +$$
$$(\text{TG/HDL-C} \times 0.101) + (BMI \times 0.0711)$$

$$P(IR) = \frac{e^{-4.056+0.9998 \times RS}}{1 + e^{-4.056+0.9998 \times RS}} \quad (2.2)$$

In some embodiments, insulin resistance is diagnosed if steady-state plasma glucose (SSPG) concentration is in the top tertile of a given population. In some embodiments, insulin resistance is diagnosed if SSPG concentration is ≥190 mg/dL. In some embodiments, insulin resistance is diagnosed if SSPG concentration is ≥195 mg/dL. In some embodiments, insulin resistance is diagnosed if SSPG concentration is ≥198 mg/dL. In some embodiments, insulin resistance is diagnosed if SSPG concentration is ≥200 mg/dL. In some embodiments, insulin resistance is diagnosed if SSPG concentration is ≥205 mg/dL.

In some embodiments, insulin resistance is diagnosed by a combination of insulin and C-peptide values determined by the mass spectrometry method described herein. In some embodiments, insulin resistance is diagnosed by a combination of insulin and C-peptide values determined by the mass spectrometry method described herein. In some embodiments, insulin resistance is diagnosed by a combination of insulin and C-peptide values determined by the mass spectrometry method described herein and SSPG concentration.

In some embodiments, the amount of the one or more ions determined is used to determine the amount of insulin and C-peptide in the sample. In some embodiments, the amount of insulin and C-peptide in the sample is related to the amount of insulin in the patient.

In some embodiments, methods comprise (a) subjecting a sample to an enrichment process to obtain a fraction enriched in insulin and C-peptide, (b) subjecting the enriched insulin and C-peptide to an ionization source under conditions suitable to generate one or more insulin and C-peptide ions detectable by mass spectrometry; (c) determining the amount of one or more insulin and C-peptide ions by mass spectrometry. In some embodiments, the amount of the one or more ions determined is used to determine the amount of insulin and C-peptide in the sample. In some embodiments, the amount of insulin and C-peptide in the sample is related to the amount of insulin in the patient. In some embodiments, the amount of insulin and C-peptide in the sample is used to determine the ratio of insulin to C-peptide in the patient.

In some embodiments, the enrichment process provided herein comprises immunocapture of insulin and C-peptide using antibodies. In some embodiments, methods comprise (a) immunocapturing insulin and C-peptide, (b) subjecting the immunocaptured insulin and C-peptide to an ionization source under conditions suitable to generate one or more insulin and C-peptide ions detectable by mass spectrometry; (c) determining the amount of one or more insulin and C-peptide ions by mass spectrometry.

In some embodiments, immunocapturing provided herein comprises using anti-insulin antibodies and anti-C-peptide antibodies. In some embodiments, the antibodies provided herein are monoclonal antibodies. In some embodiments, the antibodies provided herein are mouse monoclonal antibodies. In some embodiments, the antibodies provided herein are monoclonal IgG antibodies. In some embodiments, the antibodies provided herein are polyclonal antibodies.

In some embodiments, the anti-insulin antibodies and anti-C-peptide antibodies are immobilized on magnetic beads. In some embodiments, insulin and C-peptide immunocaptured on magnetic beads are washed and eluted.

In some embodiments, serum is delipidated prior to quantitation by mass spectrometry. In some embodiments, one or more delipidation reagent is used to remove lipids from the sample. In some embodiments, the delipidation reagent is CLEANASCITE®.

In some embodiments, the methods provided herein comprise purifying the samples prior to mass spectrometry. In some embodiments, the methods comprise purifying the samples using liquid chromatography. In some embodiments, liquid chromatrography comprise high performance liquid chromatography (HPLC) or high turbulence liquid chromatograph (HTLC). In some embodiments, the methods comprise subjecting a sample to solid phase extraction (SPE).

In some embodiments, mass spectrometry comprises tandem mass spectrometry. In some embodiments, mass spectrometry is high resolution mass spectrometry. In some embodiments, mass spectrometry is high resolution/high accuracy mass spectrometry.

In some embodiments, ionization is by electrospray ionization (ESI). In some embodiments, ionization is by atmospheric pressure chemical ionization (APCI). In some embodiments, said ionization is in positive ion mode.

In some embodiments, methods provided herein comprise adding internal standards to the sample. In some embodiments, the internal standard for insulin is bovine insulin. In some embodiments, the internal standard for C-peptide is C-peptide heavy internal standard. In some embodiments, the internal standard is labeled. In some embodiments, the internal standard is deuterated or isotopically labeled.

In some embodiments, the patient sample is a serum sample. In some embodiments, the patient sample is a plasma sample. In some embodiments, the patient sample is a blood, saliva, or urine sample.

In some embodiments, the sample is subjected to acidic conditions prior to ionization. In some embodiments, subjecting the sample to acidic conditions comprises subjecting enriched insulin and C-peptide to formic acid.

In some embodiments, the sample is subjected to basic conditions prior to mass spectrometry. In some embodiments, subjecting the sample to basic conditions comprises subjecting the sample to trizma. In some embodiments, subjecting the sample to basic conditions comprises subjecting the sample to trizma and ethanol.

In some embodiments, one or more ions comprise an insulin precursor ion with a mass to charge ratio (m/z) of $968.7 \pm 0.5$. In some embodiments, one or more ions comprise one or more fragment ions selected from the group consisting of ions with m/z of $136.0 \pm 0.5$, $226.1 \pm 0.5$, and $345.2 \pm 0.5$. In some embodiments, the insulin fragment ion with m/z of $226.1 \pm 0.5$ is the quantifier ion. In some embodiments, one or more ions comprise a bovine insulin precursor ion with a mass to charge ratio (m/z) of $956.8 \pm 0.5$. In some embodiments, one or more ions comprise one or more fragment ions selected from the group consisting of ions with m/z of $136.0 \pm 0.5$, $226.1 \pm 0.5$, and $315.2 \pm 0.5$. In some embodiments, the bovine insulin fragment ion with m/z of $136.0 \pm 0.5$ is the quantifier ion.

In some embodiments, one or more ions comprise a C-peptide precursor ion with a mass to charge ratio (m/z) of $1007.7 \pm 0.5$. In some embodiments, one or more ions comprise one or more fragment ions selected from the group consisting of ions with m/z of $533.3 \pm 0.5$, $646.4 \pm 0.5$, and $927.5 \pm 0.5$. In some embodiments, any of the C-peptide fragment ion with m/z of $533.3 \pm 0.5$, $646.4 \pm 0.5$, and $927.5 \pm 0.5$ or their summed intensity can be used for quantification. In some embodiments, one or more ions comprise a C-peptide heavy internal standard precursor ion with a mass to charge ratio (m/z) of $1009.5 \pm 0.5$. In some embodiments, one or more ions comprise one or more fragment ions selected from the group consisting of ions with m/z of $540.3 \pm 0.5$, $653.4 \pm 0.5$, and $934.5 \pm 0.5$. In some embodiments, any of the C-peptide heavy internal standard fragment ion with m/z of $540.3 \pm 0.5$, $653.4 \pm 0.5$, and $934.5 \pm 0.5$ or their summed intensity can be used for quantification.

In some embodiments, provided herein is utilizing mass spectrometry for determining the amount of insulin and C-peptide in a sample, the methods include: (a) enriching insulin and C-peptide and in a sample by an extraction technique; (b) subjecting the purified insulin and C-peptide from step (a) to liquid chromatography to obtain a fraction enriched in insulin and C-peptide from the sample; (c) subjecting the enriched insulin to an ionization source under conditions suitable to generate an insulin precursor ion detectable by mass spectrometry; and (d) determining the amount of one or more of the fragment ions by mass spectrometry. In some embodiments, the amount of the one or more ions determined is used to determine the amount of insulin and C-peptide in the sample. In some embodiments, the amount of insulin and C-peptide in the sample is related to the amount of insulin in the patient. In some embodiments, the amount of insulin and C-peptide in the sample is used to determine the ratio of insulin to C-peptide in the patient.

In some embodiments, the extraction technique provided herein comprises immunocapture of insulin and C-peptide using antibodies. In some embodiments, the extraction technique provided herein comprises solid phase extraction (SPE).

In some embodiments, the collision energy is within the range of about 40 to 60 V. In some embodiments, the collision energy is within the range of about 40 to 50 V.

In another aspect, provided herein are methods for determining the amount of insulin or C-peptide in a sample by mass spectrometry comprising (a) immunocapturing insulin or C-peptide, (b) subjecting the immunocaptured insulin or C-peptide to an ionization source under conditions suitable to generate one or more insulin or C-peptide ions detectable by mass spectrometry; (c) determining the amount of one or more insulin or C-peptide ions by mass spectrometry. In some embodiments, provided herein are methods for determining the amount of insulin in a sample by mass spectrometry comprising (a) immunocapturing insulin, (b) subjecting the immunocaptured insulin to an ionization source under conditions suitable to generate one or more insulin ions detectable by mass spectrometry; (c) determining the amount of one or more insulin ions by mass spectrometry. In some embodiments, provided herein are methods for determining the amount of C-peptide in a sample by mass spectrometry comprising (a) immunocapturing C-peptide, (b) subjecting the immunocaptured C-peptide to an ionization source under conditions suitable to generate one or more C-peptide ions detectable by mass spectrometry; (c) determining the amount of one or more C-peptide ions by mass spectrometry. In some embodiments, immunocapturing comprises using anti-insulin antibodies or anti-C-peptide antibodies. In some embodiments, the anti-insulin antibodies or anti-C-peptide antibodies are immobilized on magnetic beads. In some embodiments, insulin or C-peptide immunocaptured on magnetic beads are washed and eluted.

In another aspect, provided herein are methods for diagnosis of other glycemic disorders in diabetic and pre-diabetic patients. In some embodiments, the methods of quantitation of endogenous insulin and C-peptide provided herein are used for diagnosing diabetes. In some embodiments, the methods of quantitation of endogenous insulin and C-peptide provided herein are used for distinguishing insulin-secreting tumors from exogenous insulin administration as a cause for hypoglycemia. In some embodiments, the methods of quantitation of endogenous insulin and C-peptide provided herein are used for distinguishing type 1 diabetes from type 2 diabetes. In some embodiments, the methods of quantitation of endogenous insulin and C-peptide provided herein are used for assessing the risk of diabetes in pre-diabetic patients.

In some embodiments, mass spectrometry comprises tandem mass spectrometry. In some embodiments, mass spectrometry is high resolution mass spectrometry. In some embodiments, mass spectrometry is high resolution/high accuracy mass spectrometry.

In another aspect, certain methods presented herein utilize high resolution/high accuracy mass spectrometry to determine the amount of insulin in a sample. In some embodiments utilizing high accuracy/high resolution mass spectrometry, the methods include: (a) subjecting insulin from a sample to an ionization source under conditions suitable to generate multiply charged insulin ions, wherein the insulin ions are detectable by mass spectrometry; and (b) determining the amount of one or more multiply charged insulin ions by high resolution/high accuracy mass spectrometry. In these embodiments, the amount of one or more ions determined in step (b) is related to the amount of insulin in the sample. In some embodiments, high resolution/high accuracy mass spectrometry is conducted at a FWHM of 10,000 and a mass accuracy of 50 ppm. In some embodiments, high resolution/high accuracy mass spectrometry is conducted with a high resolution/high accuracy time-of-flight (TOF) mass spectrometer. In some embodiments, the ionization conditions comprise ionization of insulin under acidic conditions. In some related embodiments, the acidic conditions comprise treatment of said sample with formic acid prior to ionization. In some embodiments, the multiply charged insulin ions are selected from the group consisting of 4+, 5+, and 6+ charged insulin ions.

In some embodiments, one or more insulin ions in a 6+ charge state comprise one or more ions with m/z within the range of about 968.8±1.5. In some embodiments, one or more insulin ions in a 6+ charge state comprise one or more ions selected from the group consisting of ions with m/z of 968.28±0.1, 968.45±0.1, 968.62±0.1, 968.79±0.1, 968.95±0.1, 969.12±0.1, 969.28±0.1, 969.45±0.1, 969.61±0.1; such as an ions with m/z of 968.95±0.1.

In some embodiments, one or more insulin ions in a 5+ charge state comprise one or more ions with m/z within the range of about 1162.5±1.0. In some embodiments, one or more insulin ions in a 5+ charge state comprise one or more ions selected from the group consisting of ions with m/z of 1161.72 0.1, 1161.92±0.1, 1162.12±0.1, 1162.32±0.1, 1162.52±0.1, 1162.72±0.1, 1162.92±0.1, 1163.12±0.1, 1163.32±0.1; such as an ion with m/z of 1162.54±0.1.

In some embodiments, one or more insulin ions in a 4+ charge state comprise one or more ions with m/z within the range of about 1452.9±0.8.

In any of the methods described herein, the sample may comprise a biological sample. In some embodiments, the biological sample may comprise a biological fluid such as urine, plasma, or serum. In some embodiments, the biological sample may comprise a sample from a human; such as from an adult male or female, or juvenile male or female, wherein the juvenile is under age 18, under age 15, under age 12, or under age 10. The human sample may be analyzed to diagnose or monitor a disease state or condition, or to monitor therapeutic efficacy of treatment of a disease state or condition. In some related embodiments, the methods described herein may be used to determine the amount of insulin in a biological sample when taken from a human.

In embodiments utilizing tandem mass spectrometry, tandem mass spectrometry may be conducted by any method known in the art, including for example, multiple reaction monitoring, precursor ion scanning, or product ion scanning.

In some embodiments, tandem mass spectrometry comprises fragmenting a precursor ion into one or more fragment ions. In embodiments where the amounts of two or more fragment ions are determined, the amounts may be subject to any mathematical manipulation known in the art in order to relate the measured ion amounts to the amount of insulin in the sample. For example, the amounts of two or more fragment ions may be summed as part of determining the amount of insulin in the sample.

In any of the methods described herein, the analyte of interest (e.g., insulin, or chemically modified or unmodified insulin) may be purified from a sample by high performance liquid chromatography (HPLC) prior to ionization. In any of the methods described herein, the analyte of interest may be purified from a sample by an extraction technique, such as subjecting the sample to a solid phase extraction (SPE) column. In some embodiments, the extraction technique is not an immunopurification technique. Specifically, in some embodiments, the SPE column is not an immunoaffinity column. In some embodiments, immunopurification is not used at any point in the method. In some embodiments; an extraction technique and HPLC may be performed in an on-line fashion to allow for automated sample processing and analysis.

In some embodiments, the high resolution/high accuracy mass spectrometry is conducted at a resolving power (FWHM) of greater than or equal to about 10,000, such as greater than or equal to about 15,000, such as greater than or equal to about 20,000, such as greater than or equal to about 25,000. In some embodiments, the high resolution/high accuracy mass spectrometry is conducted at an accuracy of less than or equal to about 50 ppm, such as less than or equal to about 20 ppm, such as less than or equal to about 10 ppm, such as less than or equal to about 5 ppm; such as less than or equal to about 3 ppm. In some embodiments, high resolution/high accuracy mass spectrometry is conducted at a resolving power (FWHM) of greater than or equal to about 10,000 and an accuracy of less than or equal to about 50 ppm. In some embodiments, the resolving power is greater than about 15,000 and the accuracy is less than or equal to about 20 ppm. In some embodiments, the resolving power is greater than or equal to about 20,000 and the accuracy is less than or equal to about 10 ppm; preferably resolving power is greater than or equal to about 20,000 and accuracy is less than or equal to about 5 ppm, such as less than or equal to about 3 ppm.

In some embodiments, the high resolution/high accuracy mass spectrometry may be conducted with an orbitrap mass spectrometer, a time of flight (TOF) mass spectrometer, or a Fourier transform ion cyclotron resonance mass spectrometer (sometimes known as a Fourier transform mass spectrometer).

In some embodiments, the one or more insulin ions detectable by high resolution/high accuracy mass spectrometry are one or more ions selected from the group consisting of ions with m/z within the ranges of about 1452.9±0.8, 1162.5±1 and 968.8±1.5. Ions within these ranges correspond to insulin ions with charges of 4+, 5+, and 6+, respectively. Monoisotopic ions with these charges predominantly fall within the cited m/z ranges. However, lower abundance naturally occurring isotopic variants may occur outside of these ranges. Insulin ions within the range of 1162.5±1 preferably comprise an insulin ion with m/z of about 1161.72±0.1, 1161.92±0.1, 1162.12±0.1, 1162.32±0.1, 1162.52±0.1, 1162.72±0.1, 1162.92±0.1, 1163.12±0.1, 1163.32±0.1; such as an ion with m/z of 1162.54±0.1. Insulin ions within the range of 968.8±1.5 preferably comprise an insulin ion with m/z of about 968.28±0.1, 968.45±0.1, 968.62±0.1, 968.79±0.1, 968.95±0.1, 969.12±0.1, 969.28±0.1, 969.45±0.1, 969.61±0.1; such as an ions with m/z of 968.95±0.1. In some embodiments, relating the amount of one or more insulin ions detected by mass spectrometry to the amount of an insulin protein in the sample includes comparison to an internal standard; such as a human or non-human insulin protein. The internal standard may optionally be isotopically labeled.

In any of the methods presented herein, the sample may comprise a biological sample; preferably a body fluid sample, including, for example, plasma or serum.

Mass spectrometry (either tandem or high resolution/high accuracy) may be performed in positive ion mode. Alternatively, mass spectrometry may be performed in negative ion mode. Various ionization sources, including for example atmospheric pressure chemical ionization (APCI) or electrospray ionization (ESI), may be used to ionize insulin. In some embodiments, insulin, and/or chemically modified or unmodified insulin B chain are ionized by ESI in positive ion mode.

In any method presented herein, a separately detectable internal standard may be provided in the sample, the amount of which is also determined in the sample. In embodiments utilizing a separately detectable internal standard, all or a portion of both the analyte of interest and the internal standard present in the sample is ionized to produce a plurality of ions detectable in a mass spectrometer, and one or more ions produced from each are detected by mass spectrometry. In these embodiments, the presence or amount of ions generated from the analyte of interest may be related to the presence of amount of analyte of interest in the sample by comparison to the amount of internal standard ions detected.

Alternatively, the amount of insulin in a sample may be determined by comparison to one or more external reference standards. Exemplary external reference standards include blank plasma or serum spiked with human or non-human insulin, a synthetic insulin analogue, or an isotopically labeled variant thereof.

In some embodiments, the methods are capable of determining the amount of insulin in a sample at levels within the range of about 10 μIU/mL to 500 μIU/mL.

The summary of the invention described above is non-limiting and other features and advantages of the invention will be apparent from the following detailed description of the invention, and from the claims.

BRIEF DESCRIPTION OF THE DRAWINGS

FIGS. 1A-1C show odds ratio for those in the top quartile of insulin or C-peptide levels vs. those who were not in the top quartile. The odds ratios are from models that adjusted for age, sex, fasting plasma glucose, insulin, C-peptide, HDL-C, LDL-C, triglycerides, creatinine, alanine aminotransferase, body-mass index, systolic and diastolic blood pressure.

FIG. 9 shows C-peptide fragmentation and mass-to-charge ratios of ions measured.

FIG. 12 shows accuracy of controls versus calibrators adjusted for peptide content.

FIG. 16 shows summary of validation results for insulin.

FIG. 17 shows summary of validation results for C-peptide.

DETAILED DESCRIPTION OF THE INVENTION

Figure 2:
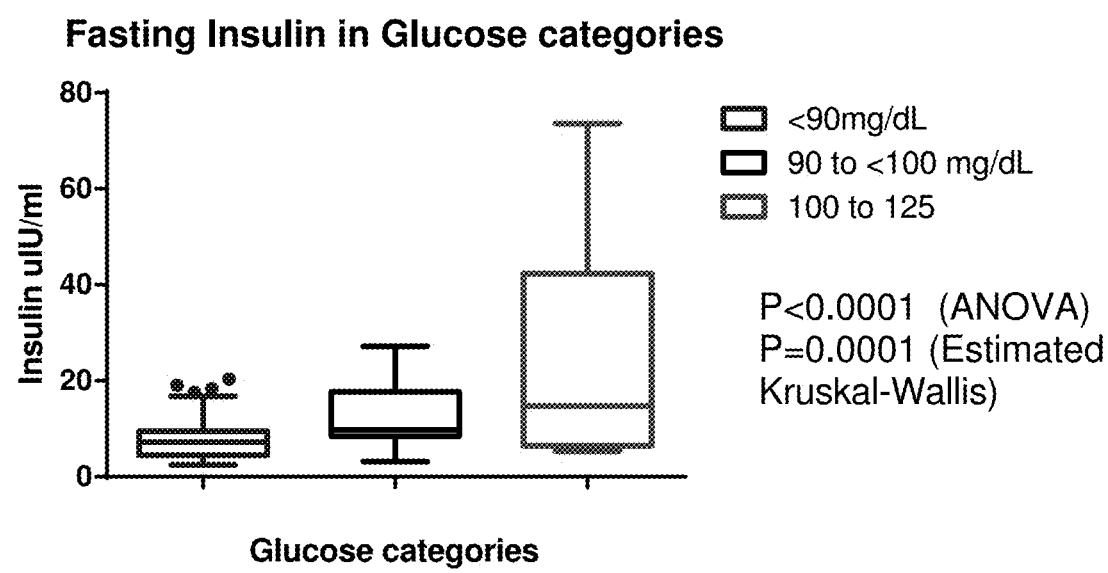
FIG. 2 shows a Box and whisker plot of fasting insulin levels in patients with fasting glucose<90 mg/dL (left), with 90 to <100 mg/dL (middle) and 100 to 125 mg/dL (right) are presented. Difference in insulin levels between categories were assessed by parametric (ANOVA) and non-parametric (Kruksal-Wallis) methods.

As used herein, unless otherwise stated, the singular forms "a," "an," and "the" include plural reference. Thus, for example, a reference to "a protein" includes a plurality of protein molecules.

As used herein, the terms "purification", "purifying", and "enriching" do not refer to removing all materials from the sample other than the analyte(s) of interest. Instead, these terms refer to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "immunopurification" or "immunopurify" refers to a purification procedure that utilizes antibodies, including polyclonal or monoclonal antibodies, to enrich the one or more analytes of interest. Immunopurification can be performed using any of the immunopurification methods well known in the art. Often the immunopurification procedure utilizes antibodies bound, conjugated or otherwise attached to a solid support, for example a column, well, tube, gel, capsule, particle or the like. Immunopurification as used herein includes without limitation procedures often referred to in the art as immunoprecipitation, as well as procedures often referred to in the art as affinity chromatography or immunoaffinity chromatography.

As used herein, the term "immunoparticle" refers to a capsule, bead, gel particle or the like that has antibodies bound, conjugated or otherwise attached to its surface (either on and/or in the particle). In certain preferred embodiments, immunoparticles are sepharose or agarose beads. In alternative preferred embodiments, immunoparticles comprise glass, plastic or silica beads, or silica gel.

As used herein, the term "anti-insulin antibody" refers to any polyclonal or monoclonal antibody that has an affinity for insulin. In various embodiments the specificity of insulin antibodies to chemical species other than insulin may vary; for example in certain preferred embodiments the anti-insulin antibodies are specific for insulin and thus have little or no affinity for chemical species other than insulin, whereas in other preferred embodiments the anti-insulin antibodies are non-specific and thus bind certain chemical species other than insulin.

As used herein, the term "sample" refers to any sample that may contain an analyte of interest. As used herein, the term "body fluid" means any fluid that can be isolated from the body of an individual. For example, "body fluid" may include blood, plasma, serum, bile, saliva, urine, tears, perspiration, and the like. In preferred embodiments, the sample comprises a body fluid sample from human; preferably plasma or serum.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit strong cation exchange and hydrophobic retention.

Generally, the affinity of a SPE column packing material for an analyte may be due to any of a variety of mechanisms, such as one or more chemical interactions or an immunoaffinity interaction. In some embodiments, SPE of insulin is conducted without the use of an immunoaffinity column packing material. That is, in some embodiments, insulin is purified from a sample by a SPE column that is not an immunoaffinity column.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., J Chromatogr A 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in substantially straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 μm. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means±10%. In a preferred embodiment the analytical column contains particles of about 5 μm in diameter.

As used herein, the terms "on-line" and "inline", for example as used in "on-line automated fashion" or "on-line extraction", refers to a procedure performed without the need for operator intervention. In contrast, the term "off-line" as used herein refers to a procedure requiring manual intervention of an operator. Thus, if samples are subjected to precipitation and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer, a mass analyzer, and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, "high resolution/high accuracy mass spectrometry" refers to mass spectrometry conducted with a mass analyzer capable of measuring the mass to charge ratio of a charged species with sufficient precision and accuracy to confirm a unique chemical ion. Confirmation of a unique chemical ion is possible for an ion when individual isotopic peaks from that ion are readily discernable. The particular resolving power and mass accuracy necessary to confirm a unique chemical ion varies with the mass and charge state of the ion.

As used herein, the term "resolving power" or "resolving power (FWHM)" (also known in the art as "$m/\Delta m_{50\%}$") refers to an observed mass to charge ratio divided by the width of the mass peak at 50% maximum height (Full Width Half Maximum, "FWHM").

As used herein a "unique chemical ion" with respect to mass spectrometry refers a single ion with a single atomic makeup. The single ion may be singly or multiply charged.

As used herein, the term "accuracy" (or "mass accuracy") with respect to mass spectrometry refers to potential deviation of the instrument response from the true m/z of the ion investigated. Accuracy is typically expressed in parts per million (ppm).

High resolution/high accuracy mass spectrometry methods of the present invention may be conducted on instruments capable of performing mass analysis with FWHM of greater than 10,000, 15,000, 20,000, 25,000, 50,000, 100,000, or even more. Likewise, methods of the present invention may be conducted on instruments capable of performing mass analysis with accuracy of less than 50 ppm, 20 ppm, 15 ppm, 10 ppm, 5 ppm, 3 ppm, or even less. Instruments capable of these performance characteristics may incorporate certain orbitrap mass analyzers, time-of-flight ("TOF") mass analyzers, or Fourier-transform ion cyclotron resonance mass analyzers. In preferred embodiments, the methods are carried out with an instrument which includes an orbitrap mass analyzer or a TOF mass analyzer.

The term "orbitrap" describes an ion trap consisting of an outer barrel-like electrode and a coaxial inner electrode. Ions are injected tangentially into the electric field between the electrodes and trapped because electrostatic interactions between the ions and electrodes are balanced by centrifugal forces as the ions orbit the coaxial inner electrode. As an ion orbits the coaxial inner electrode, the orbital path of a trapped ion oscillates along the axis of the central electrode at a harmonic frequency relative to the mass to charge ratio of the ion. Detection of the orbital oscillation frequency allows the orbitrap to be used as a mass analyzer with high accuracy (as low as 1-2 ppm) and high resolving power (FWHM) (up to about 200,000). A mass analyzer based on an orbitrap is described in detail in U.S. Pat. No. 6,995,364, incorporated by reference herein in its entirety.

As used herein, the term "operating in negative ion mode" refers to those mass spectrometry methods where negative ions are generated and detected. The term "operating in positive ion mode" as used herein, refers to those mass spectrometry methods where positive ions are generated and detected. In preferred embodiments, mass spectrometry is conducted in positive ion mode.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the ionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LOQ is identifiable, discrete and reproducible with a relative standard deviation (RSD %) of less than 20% and an accuracy of 85% to 115%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the zero concentration.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The determination of insulin in serum is primarily used for the diagnosis of glycemic disorders in diabetic and pre-diabetic patients in the assessment of insulin resistant syndromes. C-peptide is a peptide that connects insulin's 2 peptide chains and is released from proinsulin during processing and subsequently co-secreted from the pancreatic beta cell. Because of differences in half-life and hepatic clearance, peripheral blood levels of C-peptide and insulin are no longer equimolar but remain highly correlated. In the present embodiments, methods provided herein measure endogenous insulin and C-peptide for distinguishing (1) insulin-secreting tumors from exogenous insulin administration as a cause for hypoglycemia and (2) type 1 from type 2 diabetes.

In one aspect, provided herein are methods for measuring insulin levels in a patient by determining the amount of insulin and C-peptide in a sample using mass spectrometry. In some embodiments, the methods provided herein comprise multiplexed assays that simultaneously measure the amount of insulin and C-peptide in a sample by mass spectrometry. In some embodiments, methods comprise (a) subjecting insulin and C-peptide from a sample to an ionization source under conditions suitable to generate one or more insulin and C-peptide ions detectable by mass spectrometry; and (b) determining the amount of one or more insulin and C-peptide ions by mass spectrometry. In some embodiments, the amount of the one or more ions determined is used to determine the amount of insulin and C-peptide in the sample. In some embodiments, the amount of insulin and C-peptide in the sample is related to the amount of insulin in the patient. In some embodiments, the amount of insulin and C-peptide in the sample is used to determine the ratio of insulin to C-peptide in the patient.

In some embodiments, methods comprise (a) subjecting a sample to an enrichment process to obtain a fraction enriched in insulin and C-peptide, (b) subjecting the enriched insulin and C-peptide to an ionization source under conditions suitable to generate one or more insulin and C-peptide ions detectable by mass spectrometry; (c) determining the amount of one or more insulin and C-peptide ions by mass spectrometry. In some embodiments, the amount of the one or more ions determined is used to determine the amount of insulin and C-peptide in the sample. In some embodiments, the amount of insulin and C-peptide in the sample is related to the amount of insulin in the patient. In some embodiments, the amount of insulin and C-peptide in the sample is used to determine the ratio of insulin to C-peptide in the patient. In some embodiments, the enrichment process provided herein comprises immunocapture of insulin and C-peptide using antibodies. In some embodiments, methods comprise (a) immunocapturing insulin and C-peptide, (b) subjecting the immunocaptured insulin and C-peptide to an ionization source under conditions suitable to generate one or more insulin and C-peptide ions detectable by mass spectrometry; (c) determining the amount of one or more insulin and C-peptide ions by mass spectrometry. In some embodiments, immunocapturing provided herein comprises using anti-insulin antibodies and anti-C-peptide antibodies. In some embodiments, the antibodies provided herein are monoclonal antibodies. In some embodiments, the antibodies provided herein are mouse monoclonal antibodies. In some embodiments, the antibodies provided herein are monoclonal IgG antibodies. In some embodiments, the antibodies provided herein are polyclonal antibodies. In some embodiments, the anti-insulin antibodies and anti-C-peptide antibodies are immobilized on magnetic beads. In some embodiments, insulin and C-peptide immunocaptured on magnetic beads are washed and eluted.

In some embodiments, serum is delipidated prior to quantitation by mass spectrometry. In some embodiments, one or more delipidation reagent is used to remove lipids from the sample. In some embodiments, the delipidation reagent is CLEANASCITE®.

In some embodiments, the methods provided herein comprise purifying the samples prior to mass spectrometry. In some embodiments, the methods comprise purifying the samples using liquid chromatography. In some embodiments, liquid chromatography comprise high performance liquid chromatography (HPLC) or high turbulence liquid chromatograph (HTLC). In some embodiments, the methods comprise subjecting a sample to solid phase extraction (SPE).

In some embodiments, mass spectrometry comprises tandem mass spectrometry. In some embodiments, mass spectrometry is high resolution mass spectrometry. In some embodiments, mass spectrometry is high resolution/high accuracy mass spectrometry. In some embodiments, ionization is by electrospray ionization (ESI). In some embodiments, ionization is by atmospheric pressure chemical ionization (APCI). In some embodiments, said ionization is in positive ion mode.

In some embodiments, methods provided herein comprise adding internal standards to the sample. In some embodiments, the internal standard for insulin is bovine insulin. In some embodiments, the internal standard for C-peptide is C-peptide heavy internal standard. In some embodiments, the internal standard is labeled. In some embodiments, the internal standard is deuterated or isotopically labeled.

In some embodiments, the patient sample is a serum sample. In some embodiments, the patient sample is a plasma sample. In some embodiments, the patient sample is a blood, saliva, or urine sample.

In some embodiments, the sample is subjected to acidic conditions prior to ionization. In some embodiments, subjecting the sample to acidic conditions comprises subjecting enriched insulin and C-peptide to formic acid. In some embodiments, the sample is subjected to basic conditions prior to. In some embodiments, subjecting the sample to basic conditions comprises subjecting the sample to trizma. In some embodiments, subjecting the sample to basic conditions comprises subjecting the sample to trizma and ethanol.

In some embodiments, one or more ions comprise an insulin precursor ion with a mass to charge ratio (m/z) of 968.7±0.5. In some embodiments, one or more ions comprise one or more fragment ions selected from the group consisting of ions with m/z of 136.0±0.5, 226.1±0.5, and 345.2±0.5. In some embodiments, the insulin fragment ion with m/z of 226.1±0.5 is the quantifier ion. In some embodiments, one or more ions comprise a bovine insulin precursor ion with a mass to charge ratio (m/z) of 956.8±0.5. In some embodiments, one or more ions comprise one or more fragment ions selected from the group consisting of ions with m/z of 136.0±0.5, 226.1±0.5, and 315.2±0.5. In some embodiments, the bovine insulin fragment ion with m/z of 136.0±0.5 is the quantifier ion. In some embodiments, one or more ions comprise a C-peptide precursor ion with a mass to charge ratio (m/z) of 1007.7±0.5. In some embodiments, one or more ions comprise one or more fragment ions selected from the group consisting of ions with m/z of 533.3±0.5, 646.4±0.5, and 927.5±0.5. In some embodiments, any of the C-peptide fragment ion with m/z of 533.3±0.5, 646.4±0.5, and 927.5±0.5 can be used as the quantifier ion. In some embodiments, one or more ions comprise a C-peptide heavy internal standard precursor ion with a mass to charge ratio (m/z) of 1009.5±0.5. In some embodiments, one or more ions comprise one or more fragment ions selected from the group consisting of ions with m/z of 540.3±0.5, 653.4±0.5, and 934.5±0.5. In some embodiments, any of the C-peptide heavy internal standard fragment ion with m/z of 540.3±0.5, 653.4±0.5, and 934.5±0.5 can be used as the quantifier ion.

In some embodiments, provided herein is utilizing mass spectrometry for determining the amount of insulin and C-peptide in a sample, the methods include: (a) enriching insulin and C-peptide and in a sample by an extraction technique; (b) subjecting the purified insulin and C-peptide from step (a) to liquid chromatography to obtain a fraction enriched in insulin and C-peptide from the sample; (c) subjecting the enriched insulin to an ionization source under conditions suitable to generate an insulin precursor ion detectable by mass spectrometry; and (d) determining the amount of one or more of the fragment ions by mass spectrometry. In some embodiments, the amount of the one or more ions determined is used to determine the amount of insulin and C-peptide in the sample. In some embodiments, the amount of insulin and C-peptide in the sample is related to the amount of insulin in the patient. In some embodiments, the amount of insulin and C-peptide in the sample is used to determine the ratio of insulin to C-peptide in the patient. In some embodiments, the extraction technique provided herein comprises immunocapture of insulin and C-peptide using antibodies. In some embodiments, the extraction technique provided herein comprises solid phase extraction (SPE).

In some embodiments, the collision energy is within the range of about 40 to 60 eV. In some embodiments, the collision energy is within the range of about 40 to 50 eV.

In another aspect, provided herein are methods for determining the amount of insulin or C-peptide in a sample by mass spectrometry comprising (a) immunocapturing insulin or C-peptide, (b) subjecting the immunocaptured insulin or C-peptide to an ionization source under conditions suitable to generate one or more insulin or C-peptide ions detectable by mass spectrometry; (c) determining the amount of one or more insulin or C-peptide ions by mass spectrometry. In some embodiments, provided herein are methods for determining the amount of insulin in a sample by mass spectrometry comprising (a) immunocapturing insulin, (b) subjecting the immunocaptured insulin to an ionization source under conditions suitable to generate one or more insulin ions detectable by mass spectrometry; (c) determining the amount of one or more insulin ions by mass spectrometry. In some embodiments, provided herein are methods for determining the amount of C-peptide in a sample by mass spectrometry comprising (a) immunocapturing C-peptide, (b) subjecting the immunocaptured C-peptide to an ionization source under conditions suitable to generate one or more C-peptide ions detectable by mass spectrometry; (c) determining the amount of one or more C-peptide ions by mass spectrometry. In some embodiments, immunocapturing comprises using anti-insulin antibodies or anti-C-peptide antibodies. In some embodiments, the anti-insulin antibodies or anti-C-peptide antibodies are immobilized on magnetic beads. In some embodiments, insulin or C-peptide immunocaptured on magnetic beads are washed and eluted.

In another aspect, provided herein are methods for diagnosis of glycemic disorders or insulin resistant syndromes in diabetic and pre-diabetic patients. In some embodiments, the methods of quantitation of endogenous insulin and C-peptide provided herein are used for diagnosing diabetes. In some embodiments, the methods of quantitation of endogenous insulin and C-peptide provided herein are used for distinguishing insulin-secreting tumors from exogenous insulin administration as a cause for hypoglycemia. In some embodiments, the methods of quantitation of endogenous insulin and C-peptide provided herein are used for distinguishing type 1 diabetes from type 2 diabetes. In some embodiments, the methods of quantitation of endogenous insulin and C-peptide provided herein are used for assessing the risk of diabetes in pre-diabetic patients.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma and serum. Such samples may be obtained, for example, from a patient; that is, a living person, male or female, presenting oneself in a clinical setting for diagnosis, prognosis, or treatment of a disease or condition. In embodiments where the sample comprises a biological sample, the methods may be used to determine the amount of insulin in the sample when the sample was obtained from the biological source.

The present invention also contemplates kits for an insulin quantitation assay. A kit for an insulin quantitation assay may include a kit comprising the compositions provided herein. For example, a kit may include packaging material and measured amounts of an isotopically labeled internal standard, in amounts sufficient for at least one assay. Typically, the kits will also include instructions recorded in a tangible form (e.g., contained on paper or an electronic medium) for using the packaged reagents for use in an insulin quantitation assay.

Calibration and QC pools for use in embodiments of the present invention are preferably prepared using a matrix similar to the intended sample matrix, provided that insulin is essentially absent.

Sample Preparation for Mass Spectrometric Analysis

In preparation for mass spectrometric analysis, insulin may be enriched relative to one or more other components in the sample by various methods known in the art, including for example, immunocapture, liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

One method of sample purification that may be used prior to mass spectrometry is applying a sample to a solid-phase extraction (SPE) column under conditions where the analyte of interest is reversibly retained by the column packing material, while one or more other materials are not retained. In this technique, a first mobile phase condition can be employed where the analyte of interest is retained by the column, and a second mobile phase condition can subsequently be employed to remove retained material from the column, once the non-retained materials are washed through.

In some embodiments, insulin in a sample may be reversibly retained on a SPE column with a packing material comprising an alkyl bonded surface. For example, in some embodiments, a C-8 on-line SPE column (such as an Oasis HLB on-line SPE column/cartridge (2.1 mm×20 mm) from Phenomenex, Inc. or equivalent) may be used to enrich insulin prior to mass spectrometric analysis. In some embodiments, use of an SPE column is conducted with HPLC Grade 0.2% aqueous formic acid as a wash solution, and use of 0.2% formic acid in acetonitrile as an elution solution.

In other embodiments, the methods include immunopurifying insulin prior to mass spectrometry analysis. The immunopurification step may be performed using any of the immunopurification methods well known in the art. Often the immunopurification procedure utilizes antibodies bound, conjugated, immobilized or otherwise attached to a solid support, for example a column, well, tube, capsule, particle or the like. Generally, immunopurification methods involve (1) incubating a sample containing the analyte of interest with antibodies such that the analyte binds to the antibodies, (2) performing one or more washing steps, and (3) eluting the analyte from the antibodies.

In certain embodiments the incubation step of the immunopurification is performed with the antibodies free in solution and the antibodies are subsequently bound or attached to a solid surface prior to the washing steps. In certain embodiments this can be achieved using a primary antibody that is an anti-insulin antibody and a secondary antibody attached to a solid surface that has an affinity to the primary anti-insulin antibody. In alternative embodiments, the primary antibody is bound to the solid surface prior to the incubation step.

Appropriate solid supports include without limitation tubes, slides, columns, beads, capsules, particles, gels, and the like. In some preferred embodiments, the solid support is a multi-well plate, such as, for example, a 96 well plate, a 384-well plate or the like. In some embodiments the solid support are sepharose or agarose beads or gels. There are numerous methods well known in the art by which antibodies (for example, an insulin antibody or a secondary antibody) may be bound, attached, immobilized or coupled to a solid support, e.g., covalent or non-covalent linkages adsorption, affinity binding, ionic linkages and the like. In some embodiments antibodies are coupled using CNBr, for example the antibodies may be coupled to CNBr activated sepharose. In other embodiments, the antibody is attached to the solid support through an antibody binding protein such as protein A, protein G, protein A/G, or protein L.

The washing step of the immunopurification methods generally involve washing the solid support such that the insulin remain bound to the anti-insulin antibodies on the solid support. The elution step of the immunopurification generally involves the addition of a solution that disrupts the binding of insulin to the anti-insulin antibodies. Exemplary elution solutions include organic solutions, salt solutions, and high or low pH solutions.

Another method of sample purification that may be used prior to mass spectrometry is liquid chromatography (LC). In liquid chromatography techniques, an analyte may be purified by applying a sample to a chromatographic analytical column under mobile phase conditions where the analyte of interest elutes at a differential rate in comparison to one or more other materials. Such procedures may enrich the amount of one or more analytes of interest relative to one or more other components of the sample.

Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a partition process and may select LC, including HPLC, instruments and columns that are suitable for use with C peptide. The chromatographic analytical column typically includes a medium (i.e., a packing material) to facilitate separation of chemical moieties (i.e., fractionation). The medium may include minute particles. The particles typically include a bonded surface that interacts with the various chemical moieties to facilitate separation of the chemical moieties. One suitable bonded surface is a hydrophobic bonded surface such as an alkyl bonded or a cyano bonded surface. Alkyl bonded surfaces may include C-4, C-8, C-12, or C-18 bonded alkyl groups. In some embodiments, the chromatographic analytical column is a monolithic C-18 column. The chromatographic analytical column includes an inlet port for receiving a sample and an outlet port for discharging an effluent that includes the fractionated sample. The sample may be supplied to the inlet port directly, or from a SPE column, such as an on-line SPE column or a TFLC column. In some embodiments, an on-line filter may be used ahead of the SPE column and or HPLC column to remove particulates and phospholipids in the samples prior to the samples reaching the SPE and/or TFLC and/or HPLC columns.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytypic (i.e. mixed) mode. During chromatography, the separation of materials is effected by variables such as choice of eluent (also known as a "mobile phase"), elution mode, gradient conditions, temperature, etc.

In some embodiments, insulin in a sample is enriched with HPLC. This HPLC may be conducted with a monolithic C-18 column chromatographic system, for example, an Onyx Monolithic C-18 column from Phenomenex Inc. (50× 2.0 mm), or equivalent. In certain embodiments, HPLC is performed using HPLC Grade 0.2% aqueous formic acid as solvent A, and 0.2% formic acid in acetonitrile as solvent B.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, TFLC may be used for purification of insulin prior to mass spectrometry. In such embodiments, samples may be extracted using a TFLC column which captures the analyte. The analyte is then eluted and transferred on-line to an analytical HPLC column. For example, sample extraction may be accomplished with a TFLC extraction cartridge with a large particle size (50 µm) packing. Sample eluted off of this column may then be transferred on-line to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

In some embodiments, one or more of the above purification techniques may be used in parallel for purification of insulin to allow for simultaneous processing of multiple samples. In some embodiments, the purification techniques employed exclude immunopurification techniques, such as immunoaffinity chromatography.

Detection and Quantitation of Insulin by Mass Spectrometry

Mass spectrometry is performed using a mass spectrometer, which includes an ion source for ionizing the fractionated sample and creating charged molecules for further analysis. In various embodiments, insulin may be ionized by any method known to the skilled artisan. For example, ionization of insulin may be performed by electron ionization, chemical ionization, electrospray ionization (ESI), photon ionization, atmospheric pressure chemical ionization (APCI), photoionization, atmospheric pressure photoionization (APPI), Laser diode thermal desorption (LDTD), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc. insulin may be ionized in positive or negative mode. In preferred embodiments, insulin is ionized by ESI in positive ion mode.

In mass spectrometry techniques generally, after the sample has been ionized, the positively or negatively charged ions thereby created may be analyzed to determine a mass to charge ratio (m/z). Various analyzers for determining m/z include quadrupole analyzers, ion traps analyzers, time-of-flight analyzers, Fourier transform ion cyclotron resonance mass analyzers, and orbitrap analyzers. Some exemplary ion trap methods are described in Bartolucci, et al., *Rapid Commun. Mass Spectrom.* 2000, 14:967-73.

The ions may be detected using several detection modes. For example, selected ions may be detected, i.e. using a selective ion monitoring mode (SIM), or alternatively, mass transitions resulting from collision induced dissociation or neutral loss may be monitored, e.g., multiple reaction monitoring (MRM) or selected reaction monitoring (SRM). In some embodiments, the mass-to-charge ratio is determined using a quadrupole analyzer. In a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of insulin. The relative abundance of a given ion may be converted into an absolute amount of the original analyte using calibration standard curves based on peaks of one or more ions of an internal or external molecular standard.

One may enhance the resolution of MS techniques employing certain mass spectrometric analyzers through "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples. In certain embodiments, a mass spectrometric instrument with multiple quadrupole analyzers (such as a triple quadrupole instrument) is employed to conduct tandem mass spectrometric analysis.

In certain embodiments using a MS/MS technique, precursor ions are isolated for further fragmentation, and collision activated dissociation (CAD) is used to generate fragment ions from the precursor ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In some embodiments, insulin in a sample is detected and/or quantified using MS/MS as follows. Insulin is enriched in a sample by first subjecting the sample to SPE, then to liquid chromatography, preferably HPLC; the flow of liquid solvent from a chromatographic analytical column enters the heated nebulizer interface of an MS/MS analyzer; and the solvent/analyte mixture is converted to vapor in the heated charged tubing of the interface. During these processes, the analyte (i.e., insulin) is ionized. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the m/z of an insulin ion. Precursor ions with the correct m/z are allowed to pass into the collision chamber (Q2), while unwanted ions with any other m/z collide with the sides of the quadrupole and are eliminated. Precursor ions entering Q2 collide with neutral gas molecules (such as Argon molecules) and fragment. The fragment ions generated are passed into quadrupole 3 (Q3), where the fragment ions are selected for detection.

Ionization of insulin may result in multiply charged precursor ions (such as precursor ions of 4+, 5+, 6+, etc.). Ionization conditions, particularly the pH of the buffer utilized in electrospray techniques, greatly influence the identity and quantity of insulin precursor ions generated. For example, under acidic conditions, positive electrospray ionization may predominately generate 5+ and 6+ charged insulin precursor ions with m/z of 1162.5±0.5 and 968.5±0.5, respectively. However, under basic conditions, positive electrospray ionization may predominately generate 4+ and 5+ charged insulin precursor ions with m/z of 1453.75±0.5 and 1162.94±0.5, respectively. The methods may utilize either acidic or basic conditions; preferably acidic conditions.

The methods may involve MS/MS performed in either positive or negative ion mode; preferably positive ion mode. In certain embodiments, the electrospray buffer is acidic and Q1 selects for insulin precursor ions with an m/z of about 1162.5±0.5 or 968.5±0.5. Fragmentation of either of these insulin precursor ions generates fragment ions with m/z of about 226.21±0.5, and/or 135.6±0.5. Thus, in embodiments where Q1 selects for one or more insulin precursor ions selected from the group consisting of ions with m/z of about 1162.5±0.5 and 968.5±0.5, Q3 may select one or more fragment ions selected from the group of ions with m/z of about 226.21±0.5, and 135.6±0.5. In certain embodiments, the relative abundance of a single fragment ion from a single precursor ion may be measured. Alternatively, the relative abundances of two or more fragment ions from a single precursor ion may be measured. In these embodiments, the relative abundances of each fragment ion may be subjected to any known mathematical treatment to quantitatively assess insulin originally in the sample. In other embodiments, one or more fragment ions from two or more precursor ions may be measured and utilized as above to qualitatively assess insulin originally in the sample.

Alternate modes of operating a tandem mass spectrometric instrument that may be used in certain embodiments include product ion scanning and precursor ion scanning. For a description of these modes of operation, see, e.g., E. Michael Thurman, et al., Chromatographic-Mass Spectrometric Food Analysis for Trace Determination of Pesticide Residues, Chapter 8 (Amadeo R. Fernandez-Alba, ed., Elsevier 2005) (387).

In other embodiments, a high resolution/high accuracy mass analyzer may be used for quantitative analysis of insulin according to methods of the present invention. To achieve acceptable precision for quantitative results, the mass spectrometer must be capable of exhibiting a resolving power (FWHM) of 10,000 or more, with accuracy of about 50 ppm or less for the ions of interest; preferably the mass spectrometer exhibits a resolving power (FWHM) of 18,000 or better, with accuracy of about 5 ppm or less; such as a resolving power (FWHM) of 20,000 or better and accuracy of about 3 ppm or less; such as a resolving power (FWHM) of 25,000 or better and accuracy of about 3 ppm or less. Three exemplary analyzers capable of exhibiting the requisite level of performance for insulin ions are orbitrap mass analyzers, certain TOF mass analyzers, and Fourier transform ion cyclotron resonance mass analyzers.

Elements found in biological active molecules, such as carbon, oxygen, and nitrogen, naturally exist in a number of different isotopic forms. For example, most carbon is present as $^{12}C$, but approximately 1% of all naturally occurring carbon is present as $^{13}C$. Thus, some fraction of naturally occurring molecules containing at least one carbon atom will contain at least one $^{13}C$ atom. Inclusion of naturally occurring elemental isotopes in molecules gives rise to multiple molecular isotopic forms. The difference in masses of molecular isotopic forms is at least 1 atomic mass unit (amu). This is because elemental isotopes differ by at least one neutron (mass of one neutron≈1 amu). When molecular isotopic forms are ionized to multiply charged states, the mass distinction between the isotopic forms can become difficult to discern because mass spectrometric detection is based on the mass to charge ratio (m/z). For example, two isotopic forms differing in mass by 1 amu that are both ionized to a 5+ state will exhibit differences in their m/z of only 0.2. High resolution/high accuracy mass spectrometers are capable of discerning between isotopic forms of highly multiply charged ions (such as ions with charges of ±2, ±3, ±4, ±5, or higher).

Due to naturally occurring elemental isotopes, multiple isotopic forms typically exist for every molecular ion (each of which may give rise to a separately detectable spectrometric peak if analyzed with a sensitive enough mass spectrometric instrument). The m/z ratios and relative abundances of multiple isotopic forms collectively comprise an isotopic signature for a molecular ion. In some embodiments, the m/z ratios and relative abundances for two or more molecular isotopic forms may be utilized to confirm the identity of a molecular ion under investigation. In some embodiments, the mass spectrometric peak from one or more isotopic forms is used to quantitate a molecular ion. In some related embodiments, a single mass spectrometric peak from one isotopic form is used to quantitate a molecular ion. In other related embodiments, a plurality of isotopic peaks are used to quantitate a molecular ion. In these later embodiments, the plurality of isotopic peaks may be subject to any appropriate mathematical treatment. Several mathematical treatments are known in the art and include, but are not limited to summing the area under multiple peaks, or averaging the response from multiple peaks.

In some embodiments, the relative abundance of one or more ion is measured with a high resolution/high accuracy mass spectrometer in order to qualitatively assess the amount of insulin in the sample. In some embodiments, the one or more ions measured by high resolution/high accuracy mass spectrometry are multiply charged insulin ions. These multiply charged ions may include one or more of ions with a m/z within the ranges of about 1453±0.8 (i.e., one or more monoisotopic peaks from a 4+ ion), and/or 1162±1 (i.e., one or more monoisotopic peaks from a 5+ ion), and/or about 968.8±1.5 (i.e., one or more monoisotopic peaks from a 6+ ion).

The results of an analyte assay may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of insulin. Methods of generating and using such standard curves are well known in the art and one of ordinary skill is capable of selecting an appropriate internal standard. For example, in preferred embodiments one or more forms of isotopically labeled insulin may be used as internal standards. Numerous other methods for relating the amount of an ion to the amount of the original molecule will be well known to those of ordinary skill in the art.

As used herein, an "isotopic label" produces a mass shift in the labeled molecule relative to the unlabeled molecule when analyzed by mass spectrometric techniques. Examples of suitable labels include deuterium (2H), $^{13}C$, and $^{15}N$. One or more isotopic labels can be incorporated at one or more positions in the molecule and one or more kinds of isotopic labels can be used on the same isotopically labeled molecule.

In other embodiments, insulin may be subjected to a chemical treatment to generate insulin's constituent chains prior to mass spectrometric analysis. Insulin's B-chain may be separated by any chemical treatment known in the art to cause disulfide reduction. For example, insulin may be treated with TCEP (tris(2-carboxyethyl)phosphine to reduce insulin's disulfide bridges and separate the A chain and B chain.

The following Examples serve to illustrate the invention. These Examples are in no way intended to limit the scope of the methods.

EXAMPLES

Example 1: Human Insulin Resistance Study

Human subjects were apparently healthy, self-described non-Hispanic whites without a history of cardiovascular disease were. All individuals gave written informed consent to participate in the studies.

Subjects with fasting glucose≥126 mg/dL or those taking glucose lowering medications or having a diagnosis of diabetes were excluded from the analysis.

Race and ethnicity were determined during a medical history. Weight and height were measured while individuals were wearing light clothing and no shoes. Body mass index was calculated by dividing weight in kilograms by height metered squared. Blood pressure was measured using an automatic blood pressure recorder. Prior to these measurements, subjects were seated quietly for 5 minutes in a chair with feet on the floor and arm supported at heart level. Using an appropriately sized cuff, 3 blood pressure readings were taken at 1-minute intervals and averaged. Metabolic syndrome was present if 3 of the following characteristics were present: BMI>30 kg/m2; FG>100 mg/dL; hypertension (SBP≥130 mmHg or DBP≥85 mmHg), low HDL-C (<50 mg/dL, females; <40 mg/dL, males), TG≥150 mg/dL.

Insulin-mediated glucose disposal was quantified by using the insulin suppression test (IST). Evaluation of octreotide to assess insulin-mediated glucose disposal by the insulin suppression test. One catheter was used to draw blood samples and the other to administer a 180-minute infusion of octreotide (0.27 μg/m²/min), insulin (32 mU/m²/min) and glucose (267 mg/m²/min). Blood was sampled at 10-minute intervals from 150 to 180 minutes of the infusion to determine the steady-state plasma glucose (SSPG) and steady-state plasma insulin (SSPI) concentrations. Because the SSPI concentrations are similar in all individuals during the IST, the SSPG concentration provides a direct measure of the ability of insulin to mediate disposal of an infused glucose load. Thus, the higher the SSPG concentration, the more insulin resistant the individual. Insulin-mediated glucose disposal as determined by the IST is highly correlated with that obtained with the euglycemic, hyperinsulinemic clamp technique. For the purposes of this study, IR was defined as being in the top tertile of measured insulin resistance (SSPG≥198 mg/dL). Serum samples used for the measurement of insulin and C-peptide were derived from the fasting baseline samples obtained before initiation of the IST protocol.

Analysis included 335 subjects (39% males) with a complete set of biochemical and anthropometric measurements.

In this population, 118 of 335 subjects had metabolic syndrome.

The clinical characteristics of the patient population studied categorized is shown in Table 1, in which subjects have been categorized according to their insulin resistance status. Those with insulin resistance had higher proportion of males, and higher fasting plasma glucose (FPG), insulin, C-peptide, triglycerides, alanine aminotransferase, body mass index (BMI), and systolic blood pressure. HDL-C and LDL-C were lower in those with insulin resistance.

TABLE 1

Study Population Characteristics, by insulin resistance status

| Characteristics | Insulin resistant (SSPG ≥198, n = 177) | Not insulin resistant (SSPG <198, n = 358) | P value |
|---|---|---|---|
| Age, years | 47.9 ± 11.1 | 49.3 ± 9 | 0.12 |
| Male, n | 87.0 (46.5) | 103 (29.6) | <.0001 |
| Fasting plasma glucose, mg/dL | 100.1 ± 10 | 95.4 ± 9 | <.0001 |
| Intact Insulin, µU/mL | 15.2 ± 8.1 | 6.7 ± 4.1 | <.0001 |
| C-peptide, ng/mL | 2.2 ± 0.8 | 1.3 ± 0.5 | <.0001 |
| HDL-C, mg/dL | 42.3 ± 11.2 | 49.2 ± 14.1 | <.0001 |
| LDL-C, mg/dL | 114.4 ± 28.8 | 120.5 ± 34.8 | 0.03 |
| Triglycerides, mg/dL | 133.0 (100.0-198.0) | 94.0 (67.0-141.0) | <.0001 |
| Creatinine, mg/dL | 0.9 ± 0.2 | 0.9 ± 0.2 | 0.22 |
| Alanine aminotransferase, U/L | 32.8 ± 20.4 | 27.6 ± 16.4 | 0.003 |
| Body mass index, kg/m$^2$ | 33.5 ± 5.8 | 28.7 ± 4.7 | <.0001 |
| SBP, mmHg | 125.7 ± 15.3 | 121.4 ± 16 | 0.003 |
| DBP, mmHg | 74.1 ± 9.5 | 72.6 ± 9.4 | 0.09 |

Insulin resistant was defined as SSPG levels within the top tertile (SSPG ≥198). Metabolic syndrome was defined by 3 of the following characteristics being present: BMI >30 kg/m$^2$; FG >100 mg/dL; hypertension (SBP ≥130 mmHg or DBP ≥85 mmHg), low HDL-C (<50 mg/dL, females; <40 mg/dL, males), TG ≥150 mg/dL.
Values are reported as mean ±standard deviation, or n (%), except for triglycerides which are reported as median (interquartile range).
Abbreviations:
SBP, systolic blood pressure;
DBP, diastolic blood pressure;
SSPG, steady-state plasma glucose.

Example 2: Insulin and C-Peptide Measurement

We used SSPG to assess IR in 632 non-Hispanic white participants who were non-diabetic (FG<125 mg/dL and without a diagnosis of diabetes). IR was defined as the top tertile of SSPG in this population (≥201 mg/dL).

Insulin and c-peptide were assessed by a multiplexed tandem mass spectrometry assay.

Serum was delipidated and then insulin and C-peptide were immunocaptured using antibodies immobilized on magnetic beads. The beads were washed and the peptides were eluted from the beads with acidified acetonitrile in water. Trizma base was added to enhance stability of the peptides. The processes of calibrator preparation, internal standard addition, delipidation, bead deposition, immunocapture, washing and eluting the peptides from the beads were automated, using a Hamilton STAR® robotic liquid handler.

The elution plate was transferred to a ThermoFisher TurboFlow Aria TX4 HTLC system. The sample was injected onto a hydrophilic/lipophilic balanced (HLB) capture column where insulin and C-peptide were further enriched from background contaminants. Transfer solvent was used to liberate the peptides from the extraction cartridge and transferred them to a reversed phase analytical column. An acetonitrile gradient chromatographically resolved insulin and C-peptide from the remaining background contaminants and each other.

The flow of solvent from the HPLC column was directed to the heated electrospray source of an Agilent 6490 mass spectrometer. In the mass spectrometer, only the ions with the desired mass to charge ratio were allowed to pass through the Quadrupole 1 (Q1) area into the collision chamber (Q2). Then the accelerated ions collided with neutral argon gas molecules to become small fragments. Finally, in Q3 only the selected ions were chosen to reach the detector. The intensity of the signal at the detector was proportional to the number of molecules entering the mass spectrometer. Peak area ratios were then calculated for a set of known calibrators and calibration curves are established. The calibration equation can then be used to determine the concentration of insulin and C-peptide in patient samples.

Insulin m/z of 968.7 (precursor) and 136.0, 226.1, and 345.2 (fragment) were used. C-peptide m/z of 1007.7 (precursor) and 533.3, 646.4, and 927.5 (fragment) were used.

Example 3: Intra-Assay and Inter-Assay Precision

The intra-assay precision is defined as the reproducibility of a measurement within an assay and was generated from assaying 5 replicates from QCL, QCM and QCH. The coefficient of variation (CV) for 5 replicates of a sample was used to determine if the reproducibility is acceptable (15%). Statistics performed on the results for a run determined that the reproducibility (CV) for the QC's ranged from 6.2 to 11.5% for insulin and 5.1 to 6.3% C-peptide (Table 2). Intra-assay precision can also be calculated across all assays (see 930TP5319: Assay Validation Calculator). For insulin within run CV ranged from 4.7 to 9.6% and C-peptide within run CVs ranged from 4.7 to 7.0%.

The inter-assay variation is defined as the reproducibility of measurements between assays. QCL, QCM and QCH were evaluated over 5 days. The inter-assay variation (% CV) for the pools ranged from 7.3-11.3% for insulin and 6.2 to 9.0% for C-peptide. All QC pools for insulin and C-peptide met the requirement for acceptable reproducibility of 15% CV (Table 3).

Example 4: Analytical Sensitivity (Detection Limits)

Limit of Blank (LOB): The LOB is the point at which a measured value is larger than the uncertainty associated with it and is defined arbitrarily as 2 standard deviations (SD) from the zero concentration. Selectivity is the ability of an analytical method to differentiate and quantify the analyte in the presence of other components in the sample. For selectivity, analyses of blank samples of the appropriate biological matrix (stripped serum) were obtained, tested for interference and selectivity ensured at lower limit of quantification. A blank was measured 20 times and the resulting area ratios were back calculated.

The LOB was determined to be 0.9 uIU/mL for insulin and 0.06 ng/mL for C-peptide.

Limit of Detection (LOD): The LOD is the point at which a measured value is larger than the uncertainty associated with it and is defined arbitrarily as 4 standard deviations (SD) from the Zero concentration. Selectivity is the ability of an analytical method to differentiate and quantify the analyte in the presence of other components in the sample. For selectivity, analyses of blank samples of the appropriate biological matrix (stripped serum) were obtained, tested for interference and selectivity ensured at lower limit of quantification. A blank was measured 20 times and the resulting area ratios were back calculated.

The LOD was determined to be 1.5 uIU/mL for insulin and 0.10 ng/mL for C-peptide.

Limit of Quantitation (LOQ): The LOQ is the point where measurements become quantitatively meaningful. The insulin and C-peptide responses at this LOQ are identifiable, discrete and reproducible with a precision of 20% and an accuracy of 80% to 120%. The LOQ was determined by assaying five different samples at concentration close to the expected LOQ (1.25, 2.5, 5, 10, and 20 uIU/mL for insulin and 0.11, 0.22, 0.44, 0.85, 0.17 ng/ml for C-peptide) then evaluating the intra-assay reproducibility in seven runs and inter-assay reproducibility in a further 8 runs (Table 5). 2.5 uIU/mL and 0.11 ng/mL for insulin and C-peptide, respectively are the lowest concentrations that yields acceptable performance where the 95% confidence interval for the CV remains below 20%.

The LOQ was established to be 2.5 or 3 uIU/mL for insulin and 0.11 ng/mL for C-peptide.

Example 5: Analyte Measurement Range (AMR)

Calibration Verification: Ten spiked stripped serum samples pools (calibrators' concentration are 1.25, 2.5, 5, 10, 20, 40, 80, 160, 240 and 320 uIU/mL for insulin and 0.11, 0.21, 0.43, 0.85, 1.70, 3.40, 6.80, 13.60, 20.40 and 27.20 ng/mL) were prepared and analyzed 18 times on 13 separate days.

A weighted (1/X) quadratic regression (ignoring origin) from the 18 curves yielded coefficient correlations of 0.989 or greater for insulin and 0.992 or greater for C-peptide, with an accuracy of ±20% revealing a linear range of 5 to 320 uIU/mL for insulin and 0.11 to 27.20 ng/mL for C-peptide (Table 6). Linear from 0.11-27.20 ng/mL.

Example 6: Diagnosis of Insulin Resistance

For 335 of the participants all anthropomorphic measures (age, sex, SBP, DBP and BMI) and biomarkers (FG, insulin, C-peptide, HDL-C, LDL-C, TG, creatinine, and alanine aminotransferase (ALT)) were available. Among these 335 participants, we found that FG, insulin, C-peptide, HDL-C, TG, and BMI (all P<0.0001), ALT (P=0.002), and SBP (P=0.008), and were associated with IR in a model that adjusted for age and sex. Using stepwise model selection, we found that an IR model that included only insulin, C-peptide, and BMI had an AUC of 0.89. When model selection was restricted to biomarkers, a model that included only insulin and c-peptide had an AUC of 0.88. In conclusion, in this study of non-diabetic non-Hispanic Whites, fasting serum insulin and C-peptide concentrations were both associated with measurement of IR and in combination provided highly accurate information about the prevalence of IR.

Differences in traditional risk factors between those with and without IR were assessed by the Wilcoxon rank sum test for discrete variables and by chi-square tests for continuous variables. The association between insulin and C-peptide with IR was assessed using logistic regression models that adjusted for age, sex, SBP, DBP, BMI, FG, HDL-C, LDL-C, TG, creatinine, and ALT. Risk score 1 comprised of insulin, C-peptide, and BMI. Risk score 2 comprised insulin and C-peptide. All probability values are 2-sided and 95% confidence intervals (CI) are presented. All analyses were performed using SAS version 9.2.

The association between insulin resistance and the biochemical and anthropometric measurements are shown in Table 2; all except creatinine were associated with insulin resistance (P≤0.05) after adjustment for age, sex, and ethnicity. However, only insulin, C-peptide, creatinine and BMI were associated with insulin resistance when all the biochemical and anthropometric measurements were included in the model.

TABLE 2

Association of biochemical and anthropometric measures with insulin resistance

| | Age, sex, ethnicity adjusted | | | Fully adjusted* | | |
|---|---|---|---|---|---|---|
| Variables | OR | 95% CI | P value | OR | 95% CI | P value |
| Fasting plasma glucose | 1.8 | 1.5 to 2.2 | <.0001 | 1.1 | 0.9 to 1.5 | 0.42 |
| Intact Insulin | 7.7 | 5.2 to 11.3 | <.0001 | 2.5 | 1.5 to 4.3 | 0.0005 |
| C-peptide | 7.4 | 5.1 to 10.7 | <.0001 | 3.0 | 1.8 to 5.1 | <.0001 |
| HDL-C | 0.5 | 0.4 to 0.6 | <.0001 | 0.8 | 0.6 to 1.1 | 0.24 |
| LDL-C | 0.8 | 0.7 to 1.0 | 0.05 | 0.9 | 0.7 to 1.2 | 0.42 |
| Triglycerides | 1.8 | 1.5 to 2.3 | <.0001 | 1.3 | 1.0 to 1.7 | 0.07 |
| Creatinine | 0.9 | 0.7 to 1.2 | 0.63 | 0.7 | 0.5 to 0.9 | 0.02 |
| Alanine aminotransferase | 1.4 | 1.1 to 1.7 | 0.003 | 1.0 | 0.8 to 1.3 | 0.93 |
| Body mass index | 3.0 | 2.3 to 3.9 | <.0001 | 1.5 | 1.1 to 2.0 | 0.02 |
| Systolic blood pressure | 1.4 | 1.2 to 1.8 | 0.0002 | 1.1 | 0.7 to 1.6 | 0.72 |
| Diastolic blood pressure | 1.3 | 1.0 to 1.5 | 0.03 | 1.0 | 0.7 to 1.4 | 0.77 |

Odds ratios are per 1-standard deviation.
*Adjusted for age, sex, ethnicity (Hispanics, non-Hispanic whites; others), fasting plasma glucose, insulin, C-peptide, HDL-C, LDL-C, triglycerides, creatinine, alanine aminotransferase, body-mass index, systolic and diastolic blood pressure.

TABLE 3

Association of insulin resistance risk scores with insulin resistance

| Risk Score | Unadjusted OR (95% CI) | P value | Adjusted* OR (95% CI) | P value |
|---|---|---|---|---|
| Insulin, C-peptide | 13.5 (8.5 to 21.7) | <.0001 | 9.9 (5.8 to 17.0) | <.0001 |
| Insulin, C-peptide, Creatinine | 20.8 (12.6 to 34.6) | <.0001 | 13.6 (7.9 to 23.6) | <.0001 |
| Insulin, C-peptide, Creatinine, BMI | 22.8 (13.7 to 38.2) | <.0001 | 15.1 (8.7 to 26.3) | <.0001 |

Odds ratios are for the top quartile of the risk score vs. not being in the top tertile.
*Adjusted for age, sex, ethnicity, fasting plasma glucose, LDL-C, HDL-C, triglycerides, alanine aminotransferase, systolic and diastolic blood pressure.
Coefficient for Insulin, C-peptide, Creatinine, and BMI are 0.139, 1.5971, −3.3985, and 0.0658, respectively.

As insulin, C-peptide, creatinine, and BMI represented the most important variables in our modeling, we combined these into a single risk score (Model 1). This analysis demonstrated that using this approach, individuals in the top quartile of this risk score were >15-fold more likely to have insulin resistance than those who were not in the top quartile (OR=15.1, 95% CI 8.7 to 26.3), in a model that adjusted for age, sex, ethnicity, fasting plasma glucose, LDL-C, HDL-C, triglycerides, alanine aminotransferase, as well as systolic and diastolic blood pressure (Table 3).

Recognizing that the incorporation of clinical variables into laboratory diagnostics may present operational challenges, we also examined the performance of a risk scores that included only insulin, C-peptide, and creatinine (Model 2) or insulin and C-peptide only (model 3). For the risk score incorporating insulin, C-peptide, and creatinine (Model 2), the odds of being IR for those in the top quartile of this score were slightly reduced 13.6 (95% CI 7.9 to 23.6) for those in the top quartile of the risk score vs. those that are not. Finally, the employing only the insulin and C-peptide results (Model 3), those in the top quartile of this risk score had 9-fold greater odds of being insulin resistance than those who were not (OR=9.9, 95% CI 5.8 to 17.0).

Metabolic syndrome has long been recognized as strongly associated with insulin resistance and the risk of future development of type 2 diabetes. In this study population, we found that the metabolic syndrome was also associated with insulin resistance (OR=3.7, 95% CI 2.4 to 5.8) in a model that adjusted for age, sex, ethnicity, LDL-C, creatinine, alanine aminotransferase, systolic and diastolic blood pressure. By contrast, metabolic syndrome was no longer associated with insulin resistance after further adjustment for insulin and C-peptide (OR=1.1, 95% CI 0.6-1.9) (Table 1). Notably, all 3 risk scores were associated with insulin resistance whether or not the metabolic syndrome was present (Table 4).

TABLE 4

Association of insulin resistance risk scores with insulin resistance by metabolic syndrome status

| Risk Score | With Metabolic syndrome OR (95% CI) | P value | Without metabolic syndrome OR (95% CI) | P value |
|---|---|---|---|---|
| Insulin, C-peptide | 8.2 (3.9 to 17.1) | <.0001 | 14.5 (6.1 to 34.4) | <.0001 |
| Insulin, C-peptide, Creatinine | 14.0 (6.2 to 31.9) | <.0001 | 14.4 (6.5 to 32) | <.0001 |
| Insulin, C-peptide, Creatinine, BMI | 17.7 (7.8 to 40.5) | <.0001 | 16.9 (7.3 to 39.2) | <.0001 |

Odds ratios reported for those in the top quartile of the risk score vs. those that are not.
Adjusted for age, sex, ethnicity, fasting plasma glucose, LDL-C, HDL-C, triglycerides, alanine aminotransferase, systolic and diastolic blood pressure.

The information derived from these models can be used to define the probability that an individual is insulin resistant. Table 5 displays the probability that an individual is insulin resistant at different percentiles of three different risk scores, that include either 1) C-peptide and insulin, 2) C-peptide, insulin, and creatinine, BMI, and 3) C-peptide, insulin, creatinine, and BMI. It is evident that although subtle differences exist between the models, most of the information is contained within the model that incorporates C-peptide and insulin.

TABLE 5

Probability of insulin resistance by risk score percentile

| Percentile | C-peptide, Insulin | C-peptide, Insulin, Creatinine | C-peptide, Insulin, Creatinine, BMI |
|---|---|---|---|
| 95 | 0.96 (0.92 to 0.98) | 0.97 (0.95 to 0.99) | 0.97 (0.95 to 0.99) |
| 85 | 0.71 (0.63 to 0.78) | 0.72 (0.64 to 0.78) | 0.74 (0.67 to 0.81) |
| 75 | 0.50 (0.43 to 0.56) | 0.55 (0.48 to 0.62) | 0.58 (0.51 to 0.65) |
| 50 | 0.22 (0.18 to 0.27) | 0.20 (0.16 to 0.25) | 0.20 (0.16 to 0.25) |
| 25 | 0.09 (0.06 to 0.13) | 0.08 (0.05 to 0.11) | 0.07 (0.05 to 0.1) |

Values are probability of being insulin resistant (95% CI)
The intercept and coefficient for a risk score comprising C-peptide and insulin are −4.6554 and 0.9777.
The intercept and coefficient for a risk score comprising C-peptide, insulin, and creatinine are −1.8981 and 1.0894.
The intercept and coefficient for a risk score comprising C-peptide, insulin, creatinine, and BMI are −3.8492 and 1.

FIG. 1 shows that insulin and C-peptide are associated with Insulin Resistance (IR) in Individual with and without the Metabolic Syndrome.

We have examined the ability of clinical parameters and laboratory results to predict levels of insulin resistance derived from formal measurements of insulin resistance using SSPG in a multi-ethnic cohort studied in a GCRC environment over a period of 12 years. In keeping with prior studies (REFS), a range of clinical parameters were observed to be associated with formal measures of insulin resistance, including FPG, insulin, C-peptide, HDL-C, LDL-C, triglycerides, alanine aminotransferase, body-mass index (BMI), and blood pressure, even after adjusting for age, sex, and ethnicity. Of note, most of these associations did not remain significant when adjusted for insulin and C-peptide results, suggesting that they are themselves reflections of the underlying insulin resistant state that is almost completely accounted for the adjustments in the model by the inclusion of the insulin and C-peptide levels. When the model included the measurements of insulin and C-peptide, only BMI and creatinine remained marginally significant.

A surprising finding from this study was the observation that measurement of both insulin and C-peptide contributed significantly to the ability to accurately predict the level of insulin resistance as measured using SSPG.

In this study, we have employed a multiplexed assay to measure intact insulin and C-peptide using a high-throughput liquid chromatography tandem mass spectrometry. This approach permits the definition of specific thresholds that will endure over time.

While there are many ways in which the information regarding the inferred level of insulin resistance could be conveyed, we anticipate that one of the most useful ways to express this data would be to present the probability that an individual possesses a specific threshold of insulin resistance. For this purpose, we have expressed this as probability of insulin resistance, here defined as an SSPG≥198 mg % (the top tertile). Although creatinine and BMI modify this predictive tool measurably, insulin and C-peptide account for the bulk of the information.

In summary, we have demonstrated that a model incorporating fasting and C-peptide measurements is able to predict formal measurements of the levels of insulin resistance using SSPG with good accuracy. The simplicity of the model and its validity whether or not clinical parameters or other laboratory values are available are strength of this study. Our findings suggested that such a risk score would be of value in the assessment of an individual's level of insulin resistance, whether or not clinical signs are present. These findings also suggest that such measures may also be valuable for the longitudinal assessment of subjects engaged in lifestyle or pharmacological interventions to decrease insulin resistance, assessments that are currently difficult outside of a research setting.

Insulin and C-peptide are associated with insulin resistance independently of one another and of traditional risk factors, including fasting glucose.

Insulin and C-peptide can be used to assess probability of insulin resistance assessed formally using the SSPG method in those with and without metabolic syndrome.

A risk score combining C-peptide and insulin (using standardized, traceable measurements of C-peptide and insulin) could be derived and used to provide patients with their probability of having insulin resistance.

The instant methodology of a high-throughput mass spectrometric assay which simultaneously quantifies intact insulin and C-peptide concentrations can serve as a reference point for the standardization of measurements of insulin and C-peptide, and eventually the creation of a universally acceptable, quantitative approach to the identification of insulin resistance. The current study has employed this method to measure intact insulin and C-peptide and evaluated the utility of these standardized measurements to assess insulin resistance as measured by insulin-mediated glucose disposal in non-diabetic, apparently healthy individuals. The current analysis has been applied this approach to the first cohort for which all measurements have been completed (self-identified non-Hispanic white individuals).

Example 6: Intact Insulin and C-Peptide Levels Measured by Multiplexed Mass Spectrometry Elevated insulin levels have been shown to be associated with increased risk for the development of diabetes mellitus. Although clinical tests for insulin and C-peptide have been available for decades, insulin measurements have not been broadly used in clinical practice, at least in part due to the wide range of available immunoassays and the difficulties in relating results obtained from one assay platform to those obtained from others. This shortcoming has been noted in the literature for both insulin and C-peptide. Therefore, we have developed a multiplexed mass spectrometry-based assay that measures both intact insulin and C-peptide. We investigated the relationship between insulin, C-peptide, and glucose levels in fasting serum samples from a cohort of apparently healthy volunteers.

Apparently healthy subjects provided informed consent (WIRB #20121940) and fasting venous blood samples were obtained. Glucose levels were determined using an Olympus AU2700™ chemistry-immuno analyzer (Melville, NY); insulin and C-peptide levels were determined by multiplexed mass-spectrometry assay. Anthropomorphic measurements were obtained at the time of blood collection.

This study included 103 apparently healthy volunteers (46.7% males, median age=35, median BMI=26.1). Median insulin level in this population was 8.07 µIU/ml (IQR 5.38 to 12.55); insulin was elevated (≥15 µIU/ml) in 19.4% of the subjects. Insulin levels were elevated in 50% and 40%, respectively, of those with either impaired fasting glucose or fasting glucose between 90 and <100 mg/dL; in contrast, only 9.6% of those with fasting glucose<90 mg/dL had elevated insulin levels. Median insulin levels were 14.78 µIU/ml (IQR 6.44 to 42.29) in the 10 subjects with impaired fasting glucose, 9.79 µIU/ml (8.43 to 17.70) in the 20 subjects with fasting glucose between 90 and <100 mg/dL, and 7.26 µIU/ml (4.49 to 9.47) in the 73 subjects with fasting glucose<90 mg/dL (P=0.0004 for difference between medians). Insulin levels in those with BMI>26 (median=9.17 µIU/ml, IQR 6.96 to 17.33) were higher than in those with BMI≤26 (median=6.92 µIU/ml, IQR 4.08 to 9.09; P=0.0003). Insulin and C-peptide levels were highly correlated (r=0.88).

Clinical Sample Collection and Sample Preparation

Blood was obtained from apparently healthy adult volunteers (WIRB protocol #1085473). At the time of sampling, anthropomorphic measurements were obtained. Blood was obtained using barrier-free serum preparation tubes (red top) and allowed to clot. The resulting serum was immediately processed and then stored at −80° C. until analysis. Enrichment of insulin and C-peptide from patient sera (150 µL) was performed by 2 monoclonal antibodies immobilized on magnetic beads. Samples were processed on a robotic liquid handler (Microlab STAR, Hamilton, Reno, NV).

Assays

Analytical separation of intact insulin and C-peptide from remaining matrix components prior to MS was achieved with a TurboFlow Aria TLX-4 (Thermo-Fisher, San Jose, CA), a fully automated on-line two dimensional liquid chromatography system. A 6490 Triple Quadrupole Mass Spectrometer with an iFunnel (Agilent, Santa Clara, CA) served as the MS/MS detector. Detailed descriptions of LC and MS conditions were previously described.[9] Glucose levels were determined using an Olympus AU2700™ chemistry-immuno analyzer (Melville, NY).

Statistical Analysis

Difference in insulin levels between participants with jlow (<90 mg/dL), intermediate (90 to <100 mg/dL) and high (100 to 125 mg/dL) fasting glucose levels were assessed by parametric (ANOVA), non-parametric (Kruksal-Wallis) tests. Difference in insulin levels in patients with low (<26) and high (>=26) BMI were assessed by unpaired t-test. The association of BMI with insulin was assessed in a multi-variable regression model that adjusted for age, sex, and fasting glucose level.

Median insulin levels were 7.26 µIU/ml (4.49 to 9.47) in the 73 subjects with fasting glucose<90 mg/dL, 9.79 µIU/ml (8.43 to 17.70) in the 20 subjects with fasting glucose between 90 and <100 mg/dL, and 14.78 µIU/ml (IQR 6.44 to 42.29) in the 10 subjects with impaired fasting glucose (FIG. 2).

Figure 3:
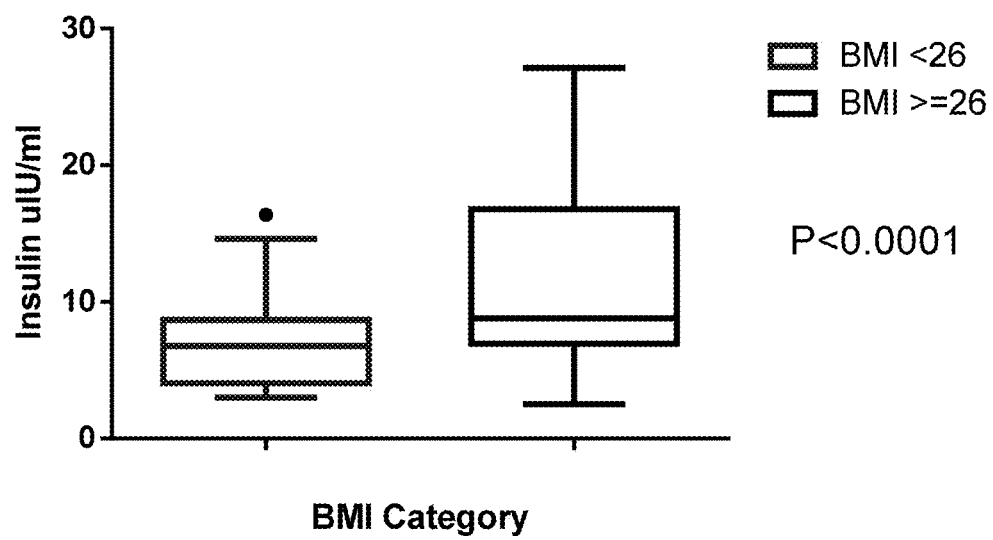
FIG. 3 shows a Box and whisker plot of fasting insulin levels in normoglycemic participants (fasting glucose<100 mg/dL) Left: BMI<26; Right: BMI≥26. Difference in insulin levels between categories were assessed by t-test.

Insulin levels in those with BMI>26 (median=9.17 µIU/ml, IQR 6.96 to 17.33) were higher than in those with BMI≤26 (median=6.92 µIU/ml, IQR 4.08 to 9.09; P=0.0003) (FIG. 3).

Figure 4:
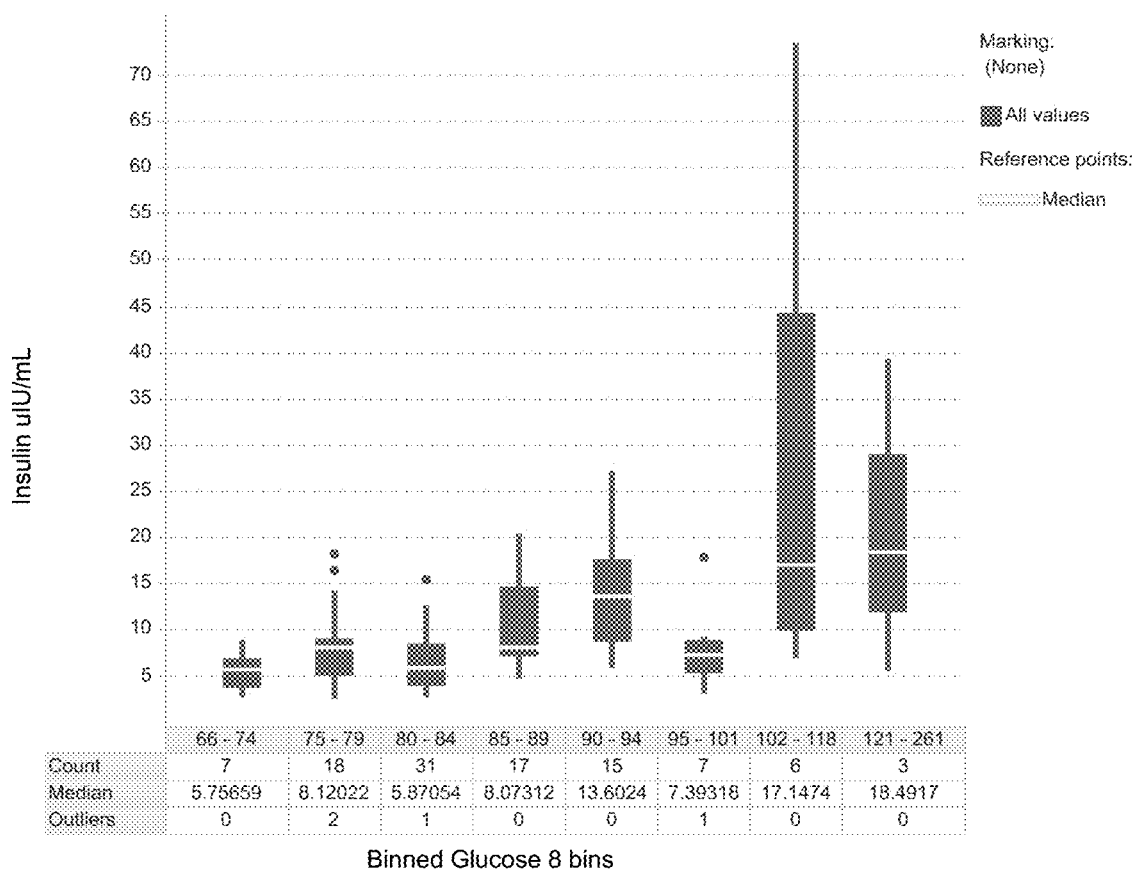
FIG. 4 shows the relationship between fasting blood glucose measurements and fasting insulin levels.
Figure 5:
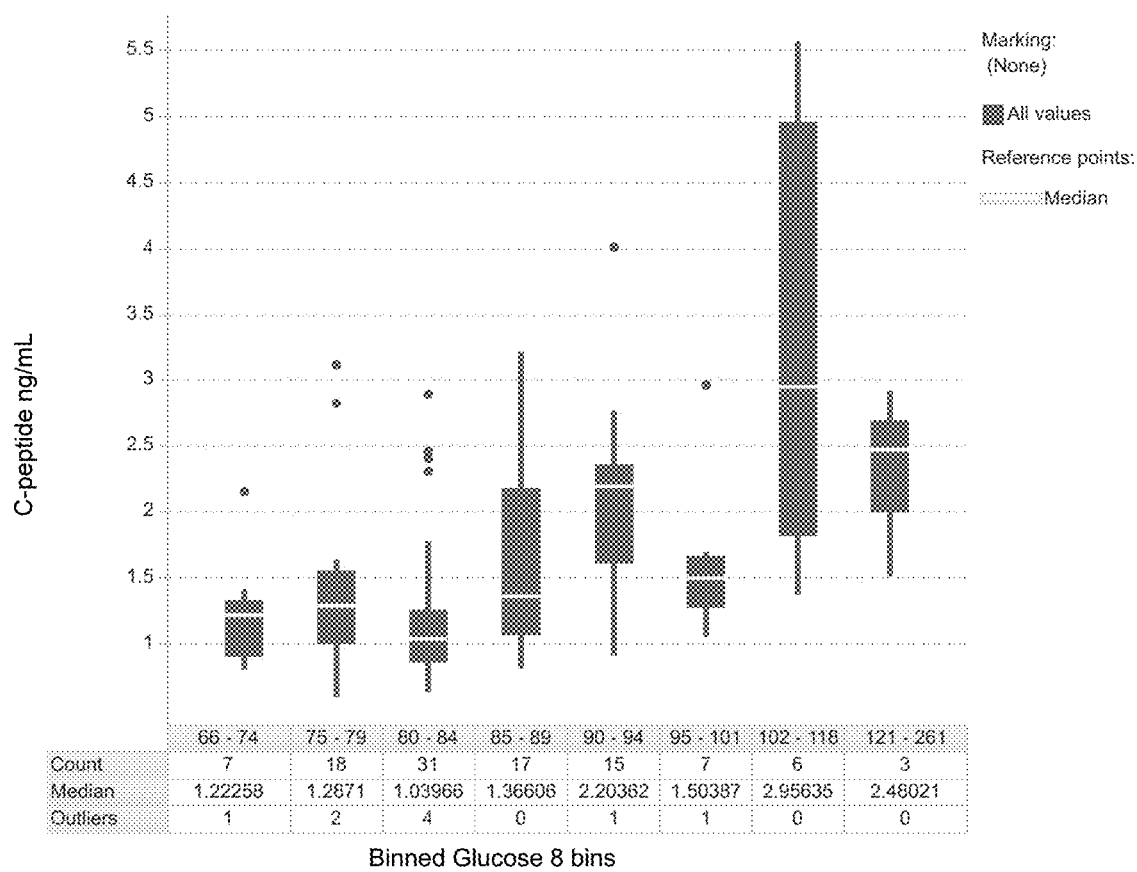
FIG. 5 shows the relationship between fasting blood glucose measurements and fasting C-peptide levels.

Insulin and C-peptide levels were found to increase as a function of fasting glucose (FIGS. 4 and 5).

Figure 6:
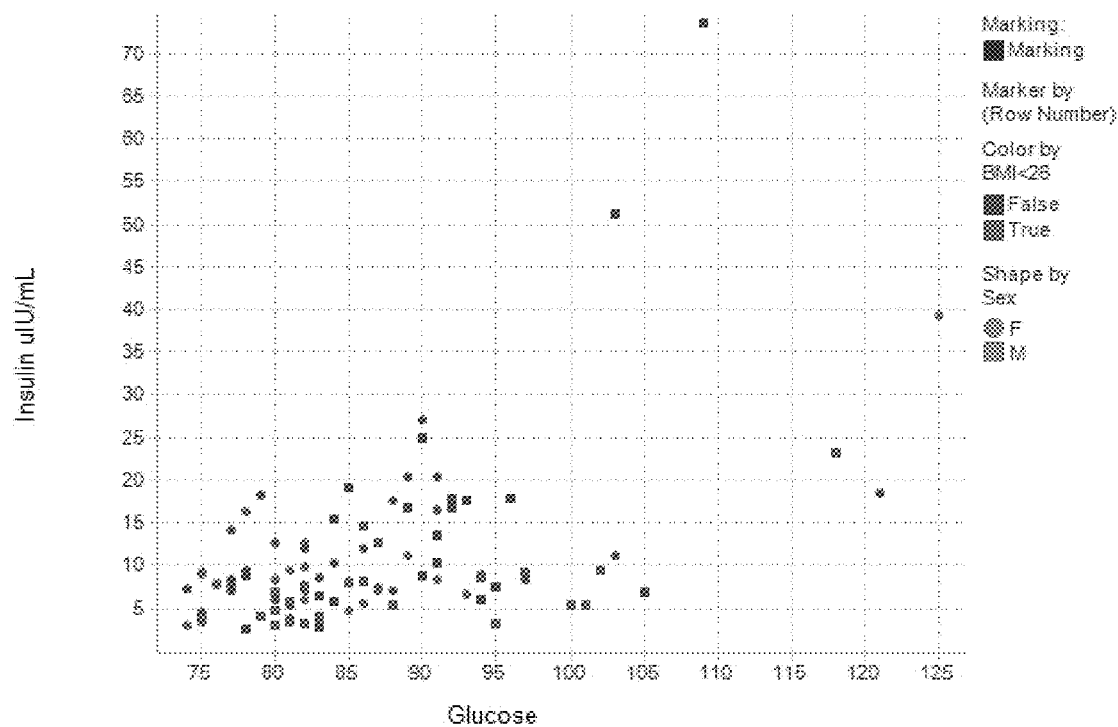
FIG. 6 shows insulin levels according to BMI category, sex, and fasting glucose.
Figure 7:
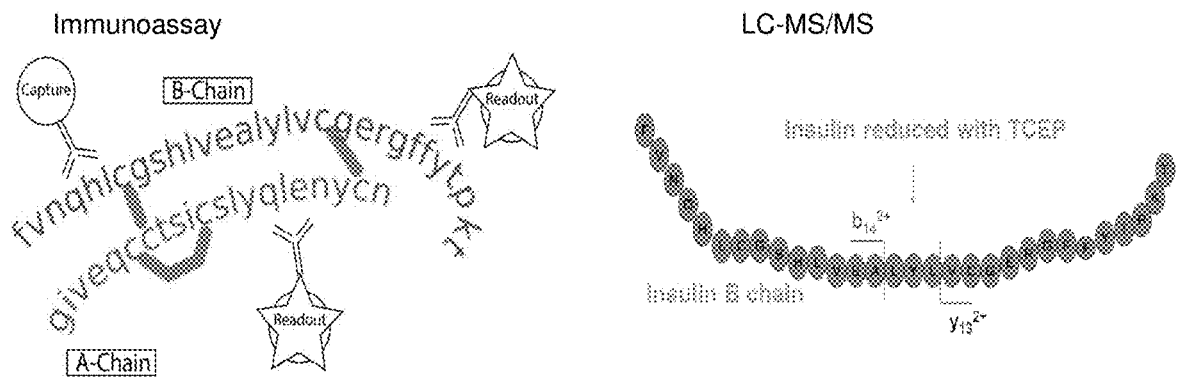
FIG. 7 shows a summary of a method presented herein.
Figure 8:
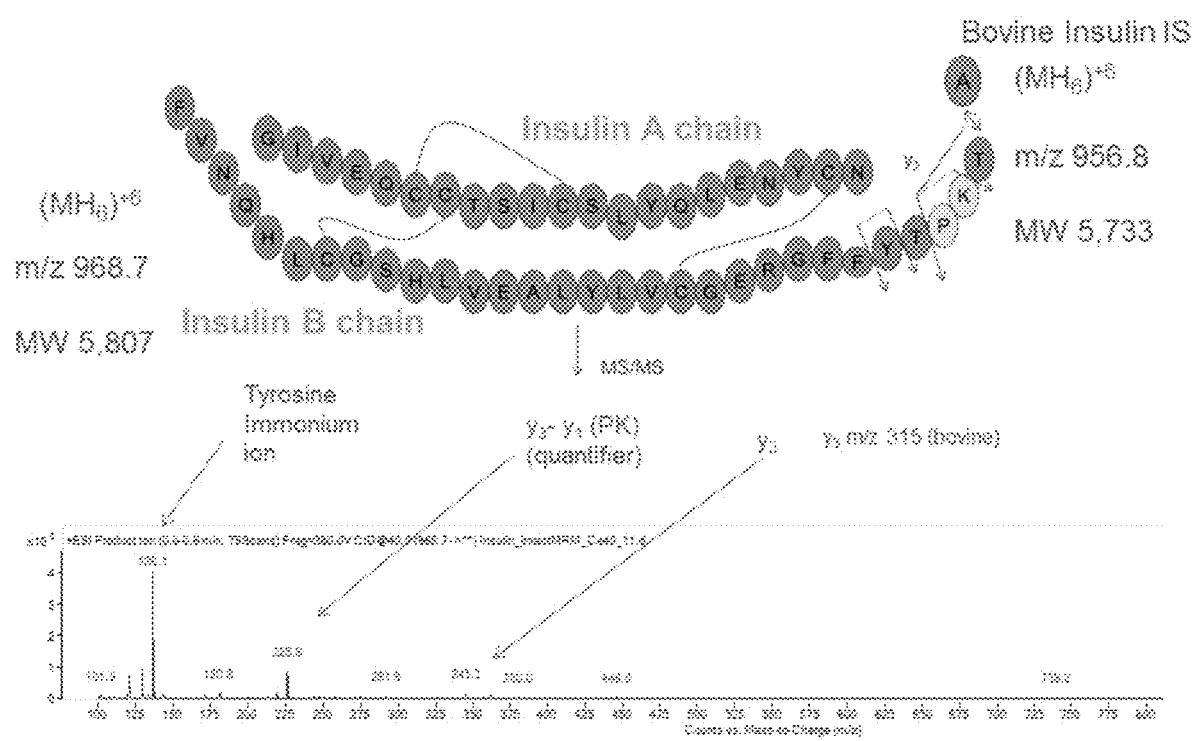
FIG. 8 shows intact insulin fragmentation and mass-to-charge ratios of ions measured.
Figure 10:
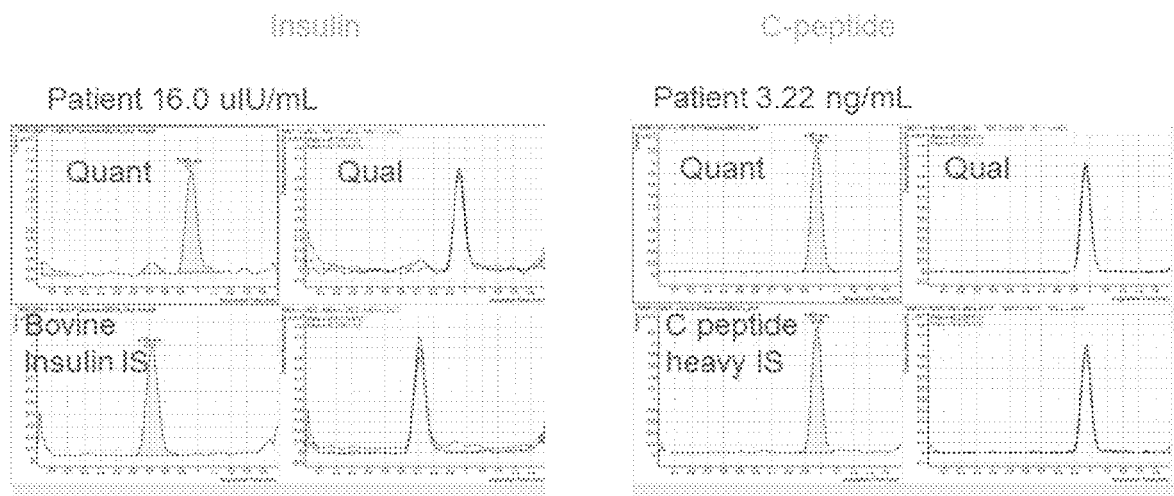
FIG. 10 shows insulin and C-peptide chromatography.
Figure 11:
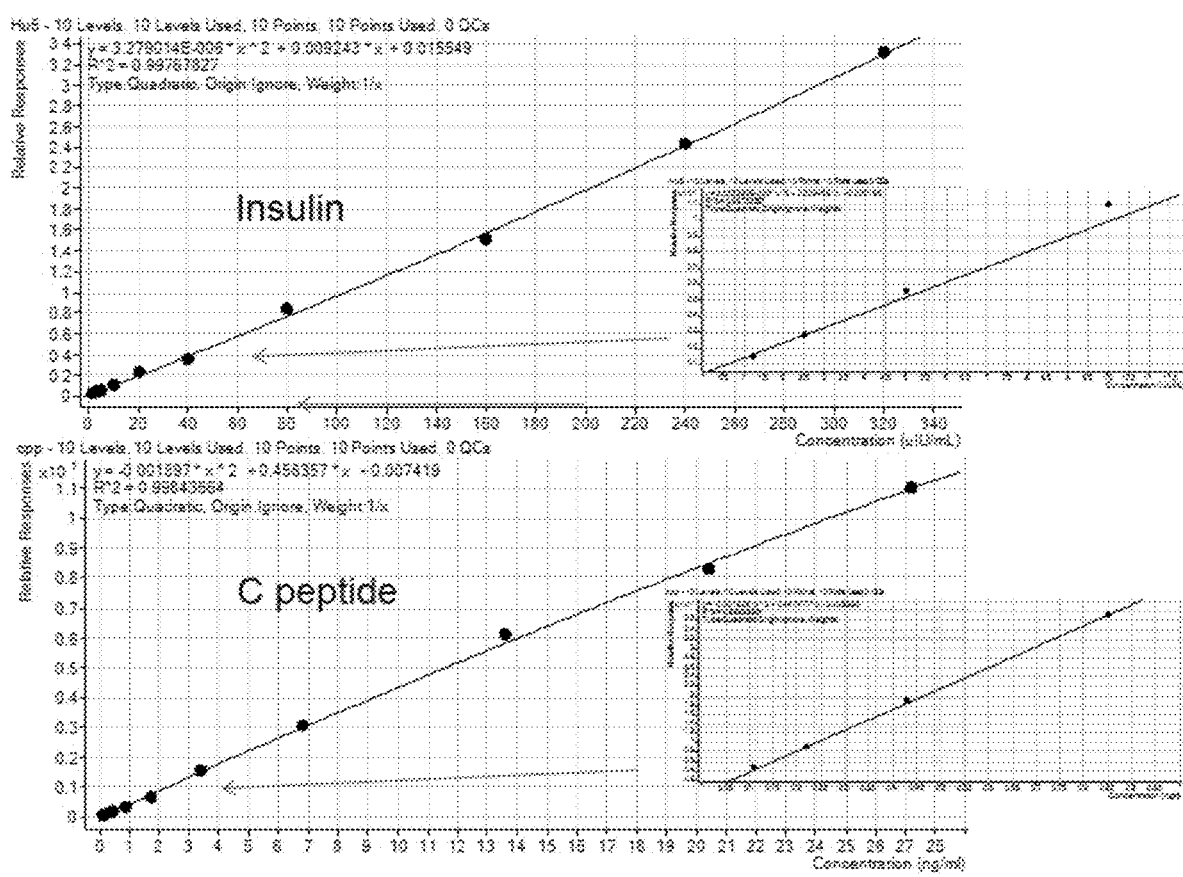
FIG. 11 shows insulin and C-peptide standard curves.
Figure 13:
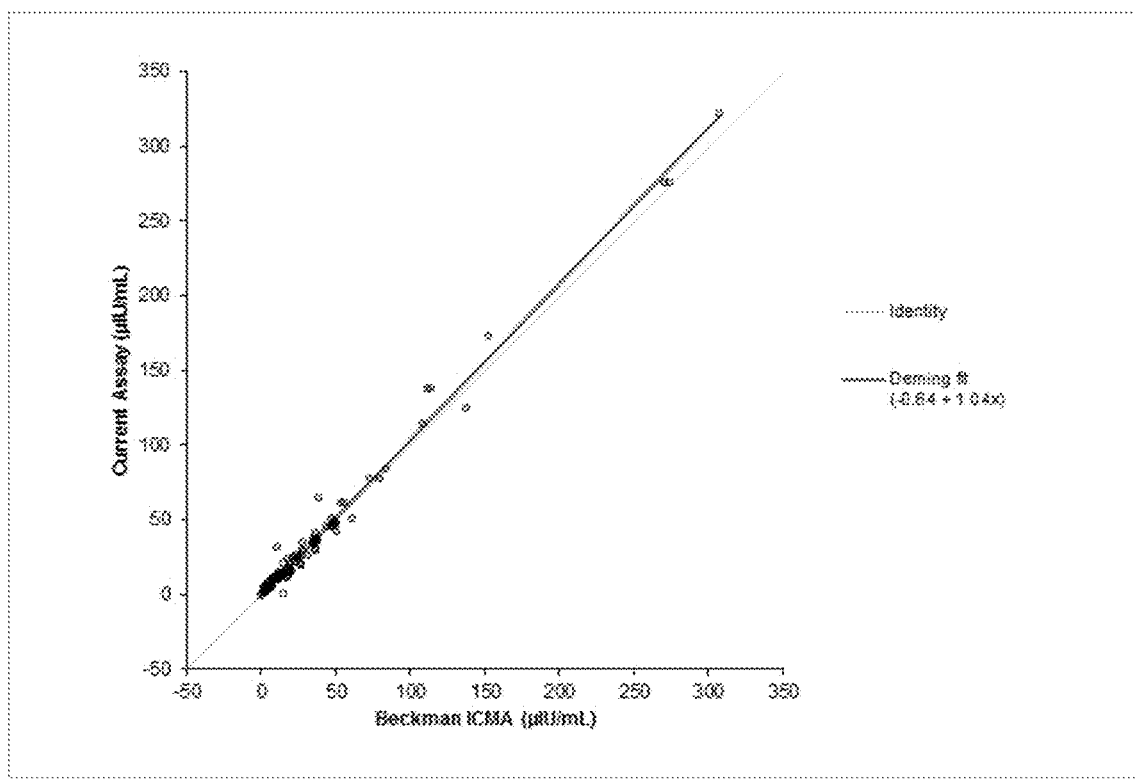
FIG. 13 shows insulin correlations (n=117) of method presented herein versus Beckman assay.
Figure 14:
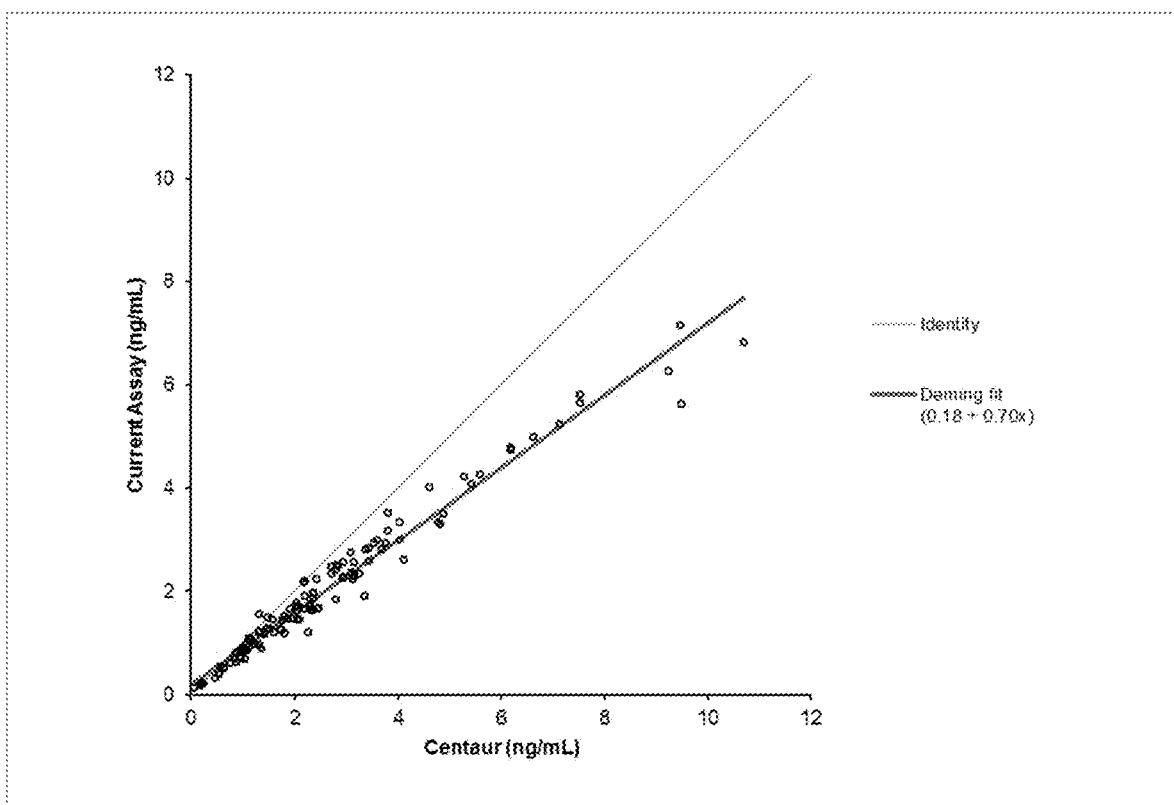
FIG. 14 shows C-peptide correlations (n=121) of method presented herein versus Centaur ICMA assay.
Figure 15:
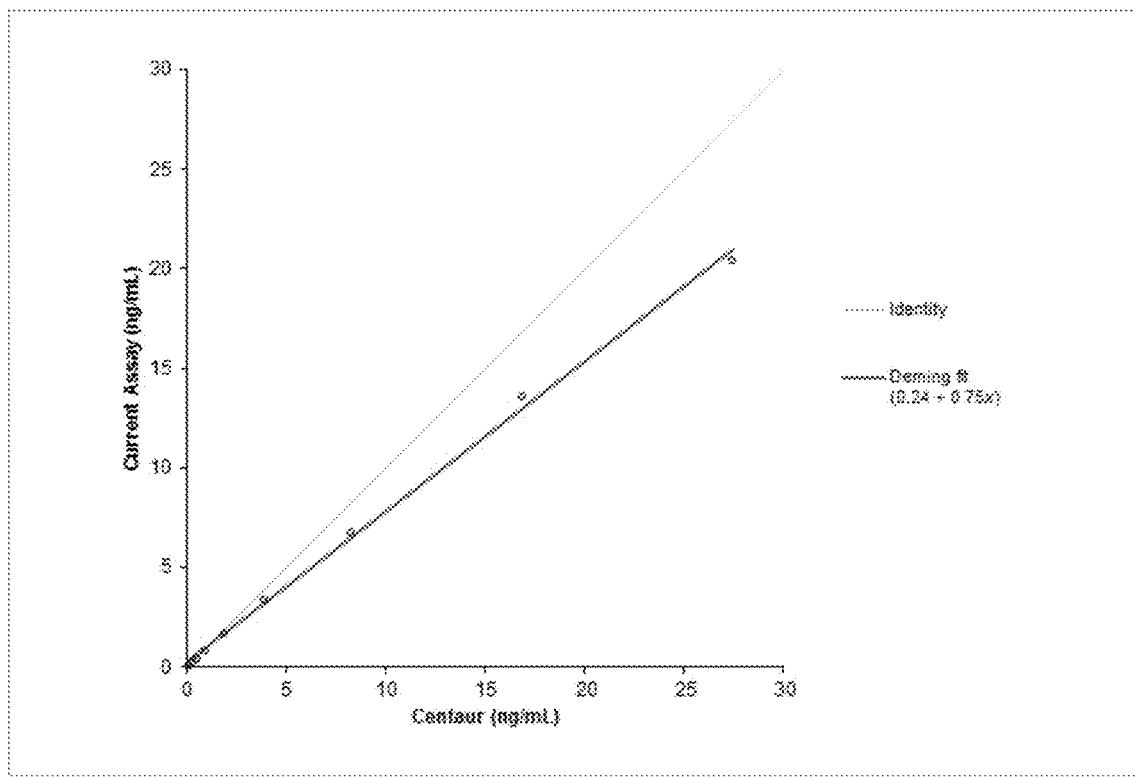
FIG. 15 shows C-peptide calibrators in Centaur ICMA.

In a multivariable regression model, BMI was associated with fasting insulin after adjustment for age, sex, and fasting glucose (P=0.00002). For each unit of BMI increase, fasting insulin was associated with 0.59 µIU increase (95% CI 0.33 to 0.85) (FIG. 6)

Discussion

This study demonstrates the application of a multiplexed mass spectrometry-based assay to measure intact insulin and C-peptide, an assay standardized by calibration to the WHO insulin reference material 83/500, and SI traceable. Measurements of C-peptide were carefully quantified with calibrators assigned by quantitative amino acid analysis. Our findings indicate that (1) elevations of insulin are observed in a substantial number of individuals who demonstrate fasting blood glucose that are within the normal range, and (2) the proportion demonstrating elevations of insulin increase progressively at higher glucose levels within the normal range.

Conclusion

We have employed the multiplexed intact insulin and C-peptide assay to define normative ranges for both analytes.

Focusing the definition of these normal ranges to employ individuals with normal fasting glucose, normal hemoglobin A1C, and a BMI<26 yields normal ranges of <16 micro µIU/mL for insulin and 0.68 to 2.16 ng/ml for C-peptide.

Fasting levels of insulin and C-peptide increased progressively as fasting glucose increased.

Fasting insulin levels were strongly influenced by BMI.

Defining the relationship of fasting insulin and C-peptide to fasting glucose and anthropomorphic measurements in individuals with well characterized assessments of insulin resistance may define tools to permit the facile assessment of levels of insulin sensitivity.

Example 7: Identification of Insulin Resistance in Apparently Healthy Individuals by Measuring Insulin and C-Peptide Levels by Mass Spectrometry We determined that a risk score comprising insulin, C-peptide, TG/HDL ratio, creatinine, and BMI can help identifying individuals with insulin resistance among both those with and without metabolic syndrome.

All study participants were apparently healthy and without history of cardiovascular disease. Individuals with fasting glucose≥126 mg/dL or those taking glucose lowering medications at baseline were excluded from the analysis.

Race and ethnicity were determined during a medical history. Weight and height were measured while individuals were wearing light clothing and no shoes. Body mass index was calculated by dividing weight in kilograms by height metered squared. Blood pressure was measured using an automatic blood pressure recorder. Prior to these measurements, subjects were seated quietly for 5 minutes in a chair with feet on the floor and arm supported at heart level. Using an appropriately sized cuff, 3 blood pressure readings were taken at 1-minute intervals and averaged. Metabolic syndrome was present if 3 of the following characteristics were present: BMI>30 kg/m2; FG>100 mg/dL; hypertension (SBP≥130 mmHg or DBP≥85 mmHg), low HDL-C (<50 mg/dL, females; <40 mg/dL, males), TG≥150 mg/dL.

After an overnight fast, an intravenous catheter was placed in each arm. One catheter was used to draw blood samples and the other to administer a 180-minute infusion of octreotide (0.27 µg/m$^2$/min), insulin (32 mU/m$^2$/min) and glucose (267 mg/m$^2$/min). Blood was sampled at 10-minute intervals from 150 to 180 minutes of the infusion to determine the steady-state plasma glucose (SSPG) and steady-state plasma insulin (SSPI) concentrations. Because the SSPI concentrations are similar in all individuals during the IST, the SSPG concentration provides a direct measure of the ability of insulin to mediate disposal of an infused glucose load. Thus, the higher the SSPG concentration, the more insulin resistant the individual. Insulin-mediated glucose disposal as determined by the IST is highly correlated with that obtained with the euglycemic, hyperinsulinemic clamp technique. For the purposes of this study, IR was defined as being in the top tertile of measured insulin resistance (SSPG≥198 mg/dL). Serum samples used for the measurement of insulin and C-peptide were derived from the fasting baseline samples obtained before initiation of the IST protocol. Measurement of insulin and C-peptide were performed as described herein.

TABLE 1

Study population Characteristics, by insulin resistance status

| Characteristics | Insulin resistant (SSPG ≥198, n = 177) | Not insulin resistant (SSPG <198, n = 358) | P value |
| --- | --- | --- | --- |
| Age, years | 47.9 ± 11.1 | 49.3 ± 9 | 0.1 |
| Male, n | 58 (32.8) | 132 (36.9) | 0.4 |
| FG, mg/dL | 100.1 ± 10.0 | 95.4 ± 9.0 | $1.8 \times 10^{-7}$ |
| Insulin, pmol/L | 90.9 ± 48.1 | 40.3 ± 24.3 | $1.1 \times 10^{-29}$ |
| (µIU/mL) | (15.2 ± 8.1) | (6.7 ± 4.1) | |
| C-peptide, pmol/L | 725.3 ± 261.2 | 424.7 ± 170.7 | $4.8 \times 10^{-33}$ |
| (ng/mL) | (2.2 ± 0.8) | (1.3 ± 0.5) | |
| Triglycerides, mg/dL | 133 (100 to 198) | 94 (67 to 141) | $1.3 \times 10^{-7}$ |
| HDL-C, mg/dL | 42.3 ± 11.2 | 49.2 ± 14.1 | $6.2 \times 10^{-10}$ |
| TG/HDL | 3.4 (2.2 to 5.1) | 2.1 (1.2 to 3.3) | $1.7 \times 10^{-8}$ |
| LDL-C, mg/dL | 114.4 ± 28.8 | 120.5 ± 34.8 | 0.03 |
| Creatinine, mg/dL | 0.9 ± 0.2 | 0.9 ± 0.2 | 0.2 |
| AAT, U/L | 32.8 ± 20.4 | 27.6 ± 16.4 | 0.003 |
| BMI, kg/m2 | 33.5 ± 5.8 | 28.7 ± 4.7 | $4.9 \times 10^{-19}$ |

TABLE 1-continued

Study population Characteristics, by insulin resistance status

| Characteristics | Insulin resistant (SSPG ≥198, n = 177) | Not insulin resistant (SSPG <198, n = 358) | P value |
|---|---|---|---|
| SBP, mmHg | 125.7 ± 15.3 | 121.4 ± 16 | 0.003 |
| DBP, mmHg | 74.1 ± 9.5 | 72.6 ± 9.4 | 0.09 |

Insulin resistant was defined as SSPG levels within the top tertile (SSPG ≥198).
Metabolic syndrome was defined by 3 of the following characteristics being present: BMI >30 kg/m2; FG >100 mg/dL; hypertension (SBP ≥130 mmHg or DBP ≥85 mmHg), low HDL-C (<50 mg/dL, females; <40 mg/dL, males), TG ≥150 mg/dL.
Values are reported as mean ±standard deviation, or n (%), except for triglycerides which are reported as median (interquartile range).
Abbreviations:
SBP, systolic blood pressure;
DBP, diastolic blood pressure;
SSPG, steady-state plasma glucose.

Differences in biochemical and anthropometric measures between those with and without IR were assessed by Wilcoxon rank-sum test or t-test for continuous variables and by chi-square tests for discrete variables. The association of study variables with IR was assessed in logistic regression models that adjusted for the covariates indicated in the tables. Since the SSPG distribution histograms appeared different for non-Hispanic whites (n=335), Hispanics (n=42), and others (n=158) ethnicity was coded as a categorical variable for these 3 groups. Risk score components were selected in a stepwise regression. All available variables were eligible to enter the model. After a best fitting available variable among those meeting specified significance inclusion cutoff is added to a model, all candidate variables in the model are assessed and removed if their significance has been increased above a specified exclusion level. This process is repeated until no more variables can be added or removed for inclusion and exclusion cutoffs indicated in the text. Risk scores coefficients were determined in models that adjusted for age, sex, ethnicity, insulin, C-peptide, creatinine, BMI, TG/HDLC, FG, SBP, DBP, LDL-C, and alanine aminotransferase, but excluding variables that were part of the risk score. All p values are 2-sided and 95% confidence intervals are presented. All analyses were performed using SAS version 9.2.

The biochemical and anthropometric measures of the study participants are shown in Table 1 according to insulin resistance status. Insulin resistant participants had higher levels of FG, insulin, C-peptide, HDL-C, TG, TG/HDL, AAT, BMI, and SBP. Insulin resistant participants had lower levels of HDL-C and LDL-C.

We investigated the association between of study variables and insulin resistance while adjusting for age, sex, ethnicity, FG, insulin, C-peptide, LDL-C, TG/HDL, creatinine, AAT, BMI, as well as SBP and DBP (Table 2). In this fully adjusted analysis, insulin, C-peptide, creatinine, BMI, and TG/HDL were associated with insulin resistance. The odds of being insulin resistant (SSPG≥198 mg/dL) were 1.2 fold higher (95% CI 1.1 to 1.4) for each 10 pmol/L increase in insulin, regardless of the level of C-peptide and other study variables. Similarly, the odds of being insulin resistant were 1.6 fold higher (95% CI 1.3 to 2.0) for each 100 pmol/L increase in C-peptide.

Figure 18:
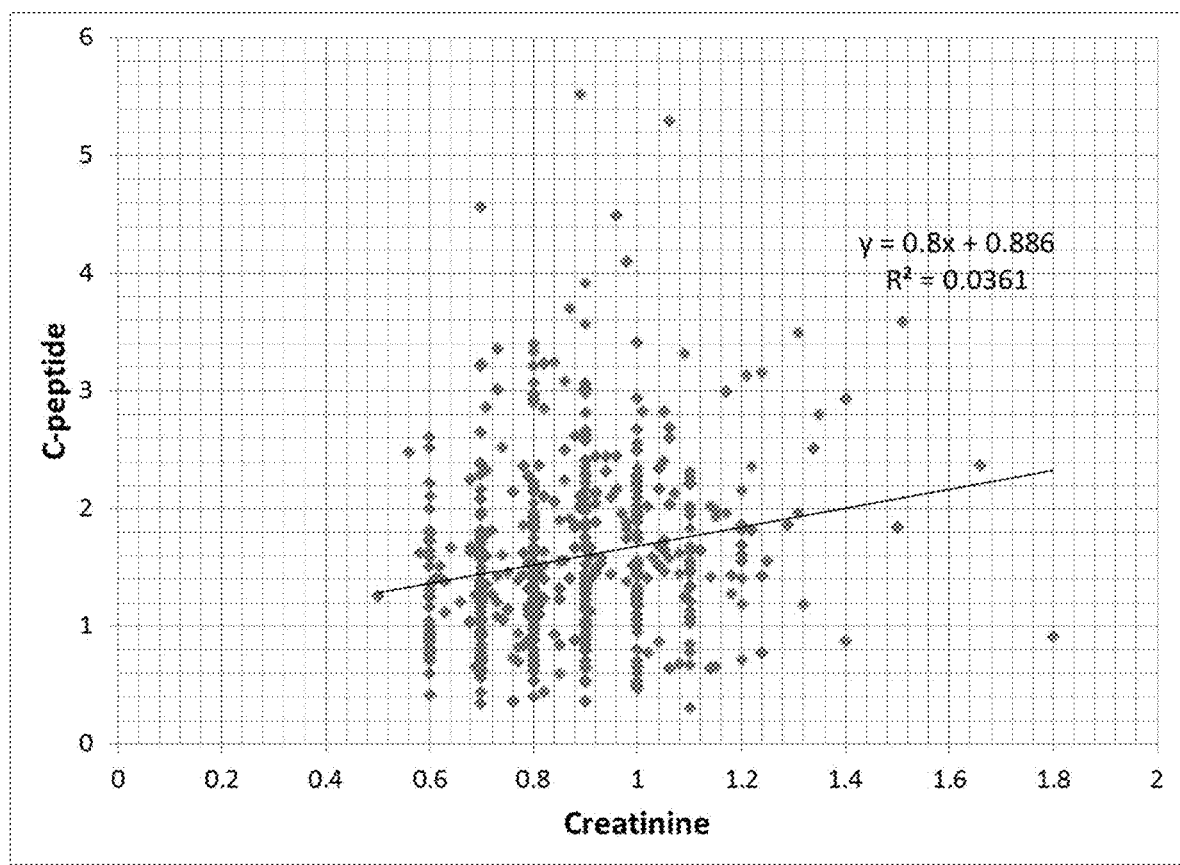
FIG. 18 shows the relationship between creatinine and C-peptide.
Figure 19:
FIG. 19 shows a sample insulin resistance score based on insulin and C-peptide levels.

Since insulin and C-peptide are highly correlated (r=0.85) we examined the prevalence of IR by tertiles of insulin and C-peptide (FIG. 18). At each insulin tertile, the fraction of IR individuals increased according to C-peptide tertile level. And conversely, at each C-peptide tertile, the fraction of IR individuals increased according to insulin tertile level.

TABLE 2

Association of biochemical and anthropometric measures with insulin resistance

| | Age, sex, ethnicity adjusted | | | Fully adjusted* | | |
|---|---|---|---|---|---|---|
| | OR | 95% CI | P value | OR | 95% CI | P value |
| FG | 1.8 | 1.5 to 2.2 | $1.2 \times 10^{-8}$ | 1.1 | 0.9 to 1.4 | 0.4 |
| Insulin | 1.6 | 1.5 to 1.8 | $3.5 \times 10^{-25}$ | 1.2 | 1.1 to 1.4 | 0.0006 |
| C-peptide | 2.2 | 1.9 to 2.6 | $3.4 \times 10^{-26}$ | 1.6 | 1.3 to 2 | $1.4 \times 10^{-5}$ |
| TG/HDL | 1.9 | 1.5 to 2.5 | $3.2 \times 10^{-8}$ | 1.4 | 1 to 1.8 | 0.03 |
| LDL-C | 0.8 | 0.7 to 1 | 0.05 | 0.9 | 0.7 to 1.2 | 0.4 |
| Creatinine | 0.9 | 0.7 to 1.2 | 0.6 | 0.7 | 0.5 to 0.9 | 0.01 |
| AAT | 1.4 | 1.1 to 1.7 | 0.003 | 1 | 0.7 to 1.3 | 0.9 |
| BMI | 3 | 2.3 to 3.9 | $4.2 \times 10^{-16}$ | 1.5 | 1.1 to 2 | 0.02 |
| SBP | 1.4 | 1.2 to 1.8 | 0.0002 | 1.1 | 0.7 to 1.5 | 0.8 |
| DBP | 1.2 | 1 to 1.5 | 0.03 | 1 | 0.7 to 1.4 | 0.9 |

Odds ratios are per 1-standard deviation.

*Adjusted for age, sex, ethnicity (Hispanics, non-Hispanic whites; others), fasting plasma glucose, insulin, C-peptide, HDL-C, LDL-C, triglycerides, creatinine, alanine aminotransferase, body-mass index, systolic and diastolic blood pressure.

TABLE 3

Association of insulin resistance markers with insulin resistance

| | Unadjusted | | Adjusted* | |
|---|---|---|---|---|
| | OR (95% CI) | P value | OR (95% CI) | P value |
| HOMA-IR | 10.3 (6.6 to 16.1) | $4.0 \times 10^{-24}$ | 1.5 (0.8 to 2.7) | 0.24 |
| Insulin | 10.9 (6.9 to 16.1) | $6.0 \times 10^{-24}$ | 1.6 (0.8 to 3.0) | 0.15 |
| C-peptide | 11.4 (7.2 to 16.1) | $1.6 \times 10^{-25}$ | 2.2 (1.1 to 4.3) | 0.023 |
| Insulin, C-peptide | 12.8 (8.0 to 16.1) | $7.0 \times 10^{-27}$ | 6.9 (3.9 to 12.1) | $1.7 \times 10^{-13}$ |
| Insulin, C-peptide, creatinine | 18.7 (11.4 to 16.1) | $3.6 \times 10^{-31}$ | 10.8 (6.2 to 19.0) | $5.6 \times 10^{-17}$ |
| Insulin, C-peptide, creatinine TG/HDL-C, BMI | 20.0 (12.1 to 16.1) | $9.2 \times 10^{-32}$ | 16.1 (9.5 to 27.3) | $9.8 \times 10^{-25}$ |

Odds ratios are for being in top quartile of variable vs. not being in the top quartile
Top quartile of insulin: >71.64 pmol/L
Top quartile of C-peptide: >652.611 pmol/L
Top quartile of HOMA-IR: >53.8667
*Adjusted for age, sex, ethnicity, insulin, C-peptide, creatinine, BMI, TG/HDLC, FG, SBP, DBP, LDL-C, and alanine aminotransferase (except for variables included in each risk score)

We used a stepwise model selection procedure to identify variables for an IR risk model among the variables in Table 2 as well as age and sex. When we used P<0.001 as criteria for variable entry and non-removal from the model, insulin, C-peptide, and creatinine were included (in that order). For individuals in the top quartile of a risk score comprising these variables (versus those not being in the top quartile), the unadjusted odds ratio for IR was 18.7 (95% CI 11.4 to 30.7, Table 3). And after adjustment for variables that were not included in the risk score, the odds ratio was 10.8 (95% CI 6.2 to 19.0). Since insulin and C-peptide can be measured in a single multiplexed test, we also examined a model that included only insulin and C-peptide and found that the unadjusted odds ratio for IR was 12.8 (95% CI 8.0 to 20.4). When more relaxed inclusion criteria for variable entry and non-removal (P<0.05) were used, 5 variables were included in the final model: insulin, C-peptide, creatinine, BMI, and TG/HDL (in that order). For individuals in the top quartile of a risk score comprising these variables the unadjusted odds ratio for IR was 20.0 (95% CI 12.1 to 33.0). After adjustment for variables that were not included in the risk score, the odds ratio was 16.1 (95% CI 9.5 to 27.3).

We also examined HOMA-IR, a commonly used method to estimate insulin resistance, and found that for those in the top quartile of HOMA-IR (vs. those not in the top quartile) the unadjusted odds ratio for IR was 10.3 (95% CI 6.6 to 16.1). After adjustment for variables that were not included in the risk score, the odds ratio was 1.5 (95% CI 0.8 to 2.7).

When the study population was limited to those with metabolic syndrome these risk scores remained associated with IR: OR=9.1 (95% CI 4.2 to 19.5) for insulin and C-peptide score, OR=13.3 (95% CI 5.9 to 30.1) for insulin, C-peptide, and creatinine score, and OR=13.7 (95% CI 6.3 to 29.9) for insulin, C-peptide, creatinine, BMI, and TG/HDL score, after adjusting each score for the variables that were not included in that score.

The clinical characteristics of the patient population studied categorized is shown in Table 1, in which subjects have been categorized according to their insulin resistance status. Those with insulin resistance had higher proportion of males, and higher fasting plasma glucose (FPG), insulin, C-peptide, triglycerides, alanine aminotransferase, body mass index (BMI), and systolic blood pressure. HDL-C and LDL-C were lower in those with insulin resistance.

We also used these risk scores to estimate the probability that an individual has IR (Table 4). Thus, rather than assigning the likelihood of being IR based on a single cut-point (e.g., whether a patient is in the top quartile of a risk score) the probability of having IR can be calculated for each percentile of the risk. For each of the 3 risk scores in Tables 3 and 4, we provided an equation that can be used to calculate the probability of being IR from measurements of risk score components.

The association between insulin resistance and the biochemical and anthropometric measurements are shown in Table 2; all except creatinine were associated with insulin resistance (P≤0.05) after adjustment for age, sex, and ethnicity. However, only insulin, C-peptide, creatinine and BMI were associated with insulin resistance when all the biochemical and anthropometric measurements were included in the model.

As insulin, C-peptide, creatinine, and BMI represented the most important variables in our modeling, we combined these into a single risk score (Model 1). This analysis demonstrated that using this approach, individuals in the top quartile of this risk score were >15-fold more likely to have insulin resistance than those who were not in the top quartile (OR=15.1, 95% CI 8.7 to 26.3), in a model that adjusted for age, sex, ethnicity, fasting plasma glucose, LDL-C, HDL-C, triglycerides, alanine aminotransferase, as well as systolic and diastolic blood pressure (Table 3).

Recognizing that the incorporation of clinical variables into laboratory diagnostics may present operational challenges, we also examined the performance of a risk scores that included only insulin, C-peptide, and creatinine (Model 2) or insulin and C-peptide only (model 3). For the risk score incorporating insulin, C-peptide, and creatinine (Model 2), the odds of being IR for those in the top quartile of this score were slightly reduced 13.6 (95% CI 7.9 to 23.6) for those in the top quartile of the risk score vs. those that are not. Finally, the employing only the insulin and C-peptide results (Model 3), those in the top quartile of this risk score had 9-fold greater odds of being insulin resistance than those who were not (OR=9.9, 95% CI 5.8 to 17.0).

In this study population, we found that the metabolic syndrome was also associated with insulin resistance (OR=3.7, 95% CI 2.4 to 5.8) in a model that adjusted for age, sex, ethnicity, LDL-C, creatinine, alanine aminotransferase, systolic and diastolic blood pressure. By contrast, metabolic syndrome was no longer associated with insulin resistance after further adjustment for insulin and C-peptide (OR=1.1, 95% CI 0.6-1.9) (Table 1). Notably, all 3 risk scores were associated with insulin resistance whether or not the metabolic syndrome was present (Table 4). And Table 4 displays the probability that an individual is insulin resistant at different percentiles

TABLE 4

Probability of insulin resistance by risk score percentile

| Percentile | Insulin, C-peptide, creatinine | Insulin, C-peptide, creatinine, TG/HDL-C, BMI | Insulin, C-peptide |
|---|---|---|---|
| 95 | 0.98 (0.95 to 0.99) | 0.97 (0.94 to 0.99) | 0.96 (0.92 to 0.98) |
| 85 | 0.73 (0.65 to 0.79) | 0.75 (0.67 to 0.81) | 0.71 (0.63 to 0.78) |
| 75 | 0.55 (0.48 to 0.62) | 0.59 (0.51 to 0.65) | 0.51 (0.45 to 0.58) |
| 50 | 0.21 (0.17 to 0.25) | 0.20 (0.16 to 0.25) | 0.21 (0.17 to 0.26) |
| 25 | 0.08 (0.05 to 0.11) | 0.07 (0.05 to 0.11) | 0.09 (0.06 to 0.12) |

Values are probability of being insulin resistant (95% CI)

Risk Scores Calculations and Probability of IR
Risk score 1: insulin (pmol/L), C-peptide (pmol/L), creatinine (mg/dL)

$$RS = (\text{Insulin} \times 0.0265) + (\text{C-peptide} \times 0.00511) + (\text{Creatinine} \times -3.2641) \quad (1.1)$$

$$P(IR) = \frac{e^{-2.2626+1.0005 \times RS}}{1 + e^{-2.2626+1.0005 \times RS}} \quad (1.2)$$

Risk score 2: insulin (pmol/L), C-peptide (pmol/L), creatinine (mg/dL), TG/HDL-C, and BMI (kg/m$^2$)

$$RS = (\text{Insulin} \times 0.0227) + (\text{C-peptide} \times 0.0046) + (\text{Creatinine} \times -3.5553) + (\text{TG/HDL-C} \times 0.101) + (BMI \times 0.0711) \quad (3.1)$$

$$P(IR) = \frac{e^{-4.056+0.9998 \times RS}}{1 + e^{-4.056+0.9998 \times RS}} \quad (2.2)$$

Risk score 3: insulin (pmol/L) and C-peptide (pmol/L)

$$RS = (\text{Insulin} \times 0.0295) + (\text{C-peptide} \times 0.00372) \quad (3.1)$$

$$P(IR) = \frac{e^{-4.5046+1.0001 \times RS}}{1 + e^{-4.5046+1.0001 \times RS}} \quad (3.2)$$

A surprisingly, finding from this study was the observation that measurement of both insulin and C-peptide contributed significantly to the ability to accurately predict the level of insulin resistance as measured using SSPG.

We have demonstrated that a model incorporating fasting and C-peptide measurements is able to predict formal measurements of the levels of insulin resistance using SSPG with good accuracy.

Those in the top quartile of a risk score comprising insulin, C-peptide, creatinine, and BMI were more likely to be IR compared with those that were not in the top quartile (OR=15.1, 95% CI 8.7 to 26.3). And this association was observed in both those with metabolic syndrome (OR=17.7, 95% CI 7.8 to 40.5) and without metabolic syndrome (OR=16.9 95% CI 7.3 to 39.2).

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for measuring insulin resistance in diabetic or pre-diabetic patients by mass spectrometry, the method comprising:
   (a) purifying a sample comprising insulin and C-peptide by liquid chromatography;
   (b) ionizing the insulin and the C-peptide by an ionization source under conditions suitable to generate one or more insulin and C-peptide ions detectable by mass spectrometry; and
   (c) determining an amount of the one or more insulin and C-peptide ions by mass spectrometry;
   (d) determining an amount of the insulin and the C-peptide in the sample from the amount of the one or more insulin and C-peptide ions; and
   (d) determining an insulin resistance score (RS) and/or a probability of developing insulin resistance (P(IR)) from the amount of the insulin and the C-peptide in the sample, wherein insulin resistance in diabetic or pre-diabetic patients is measured from the RS and/or the P(IR);
   wherein $$RS = (\text{Insulin} \times 0.0295) + (\text{C-peptide} \times 0.00372)$$

$$P(IR) = \frac{e^{-4.5046+1.0001 \times RS}}{1+e^{-4.5046+1.0001 \times RS}}.$$

2. The method of claim 1, wherein the method further comprises measuring creatinine levels.

3. The method of claim 1, wherein the method further comprises measuring body mass index (BMI).

4. The method of claim 1, wherein the method further comprises measuring triglyceride (TG) levels.

5. The method of claim 1, wherein the method further comprises measuring high density lipoprotein C (HDL-C) levels.

6. The method of claim 1, wherein the method further comprises measuring BMI, TG, and HDL-C levels.

7. The method of claim 1, wherein the sample comprises a plasma or serum sample.

8. The method of claim 1, wherein the ionization source is an electrospray (ESI) ionization source.

9. The method of claim 1, wherein the sample is subjected to acidic conditions prior to mass spectrometry.

10. The method of claim 9, wherein subjecting the sample to acidic conditions comprises subjecting the sample to formic acid.

11. The method of claim 1, wherein the sample is subjected to basic conditions prior to mass spectrometry.

12. The method of claim 11, wherein subjecting the sample to basic conditions comprises subjecting the sample to trizma and/or ethanol.

13. The method of claim 1, wherein the one or more ions comprise an insulin precursor ion has a mass to charge ratio (m/z) of 968.9±0.5.

14. The method of claim 1, wherein the one or more ions comprise one or more insulin fragment ions selected from the group consisting of ions with m/z of 136.0±0.5, 226.1±0.5, and 345.2±0.5.

15. The method of claim 1, wherein the one or more ions comprise a C-peptide precursor ion has a mass to charge ratio (m/z) of 1007.7±0.5.

16. The method of claim 1, wherein the one or more ions comprise one or more C-peptide fragment ions selected from the group consisting of ions with m/z of 533.3±0.5, 646.4±0.5, and 927.5±0.5.

17. The method of claim 1, wherein the sample is delipidated prior to quantitation by mass spectrometry.

18. The method of claim 1, wherein liquid chromatography comprises high performance liquid chromatography (HPLC) or high turbulence liquid chromatograph (HTLC).

19. The method of claim 1, wherein the purifying further comprises subjecting a sample to solid phase extraction (SPE).

20. The method of claim 1, wherein the mass spectrometry is tandem mass spectrometry, high resolution mass spectrometry, or high resolution/high accuracy mass spectrometry.

21. The method of claim 1, wherein ionization is in positive ion mode.

22. The method of claim 1, wherein an internal standard for insulin and an internal standard for C-peptide are added to the sample.

23. The method of claim 22, wherein the internal standard for insulin is bovine insulin.

24. The method of claim 23, wherein the bovine insulin comprises a precursor ion with a mass to charge ratio (m/z) of 956.8±0.5 and fragment ions selected from the group consisting of ions with a m/z of 136.0±0.5, 226.1±0.5, and 315.2±0.5.

25. The method of claim 24, wherein the internal standard for C-peptide is a C-peptide heavy internal standard.

26. The method of claim 25, wherein the C-peptide heavy internal standard comprises a precursor ion with a mass to charge ratio (m/z) of 1009.5±0.5 and fragment ions selected from the group consisting of ions with m/z of 540.3±0.5, 653.4±0.5, and 934.5±0.5.

27. The method of claim 1, wherein the amount of the insulin and the C-peptide in the sample is used to determine a ratio of insulin to C-peptide.

28. The method of claim 1 further comprising subjecting a sample to an enrichment process to obtain a fraction enriched in insulin and C-peptide.

29. The method of claim 28, wherein the enrichment process comprises an immunocapture of insulin and C-peptide.

30. The method of claim 29, wherein the immunocapture comprises using anti-insulin antibodies and anti-C-peptide antibodies.

31. The method of claim 30, wherein the anti-insulin antibodies and the anti-C-peptide antibodies are monoclonal antibodies.

32. The method of claim 31, wherein the monoclonal antibodies are monoclonal IgG antibodies.

33. The method of claim 30, wherein the anti-insulin antibodies and the anti-C-peptide antibodies are immobilized on magnetic beads.

34. The method of claim 33, wherein the insulin and the C-peptide immunocaptured on the magnetic beads are washed and eluted.

35. The method of claim 1, wherein insulin resistance is diagnosed if the amount of C-peptide is greater than or equal to 2.4 ng/mL.

36. The method of claim 1, wherein insulin resistance is diagnosed if the amount of insulin is greater than or equal to 15 µIU/mL.

37. The method of claim 1, wherein insulin resistance is diagnosed if the amount of C-peptide is greater than or equal to 2.4 ng/mL and the amount of insulin is greater than or equal to 15 µIU/mL.

* * * * *